(12) United States Patent
Tang et al.

(10) Patent No.: US 10,294,440 B2
(45) Date of Patent: *May 21, 2019

(54) CATALYTIC SYSTEM FOR PREPARATION OF HIGH BRANCHED ALKANE FROM OLEFINS

(71) Applicant: Shanghai Chemrun Co., Ltd., Shanghai (CN)

(72) Inventors: Yong Tang, Shanghai (CN); Wenjie Tao, Shanghai (CN); Xiuli Sun, Shanghai (CN); Junfang Li, Shanghai (CN); Zheng Wang, Shanghai (CN)

(73) Assignee: Shanghai Chemrun Co., Ltd., Shanghai (CN)

( * ) Notice: Subject to any disclaimer, the term of this patent is extended or adjusted under 35 U.S.C. 154(b) by 82 days.

This patent is subject to a terminal disclaimer.

(21) Appl. No.: 15/078,830

(22) Filed: Mar. 23, 2016

(65) Prior Publication Data

US 2017/0051222 A1    Feb. 23, 2017

Related U.S. Application Data

(63) Continuation of application No. 14/118,172, filed as application No. PCT/CN2012/074545 on Apr. 23, 2012, now Pat. No. 9,315,755.

(30) Foreign Application Priority Data

May 16, 2011   (CN) ........................... 2011 1 0126431
Apr. 5, 2012   (CN) ........................... 2012 1 0098399

(51) Int. Cl.
| | | |
|---|---|---|
| *C10M 105/04* | (2006.01) | |
| *B01J 31/18* | (2006.01) | |
| *C07C 323/45* | (2006.01) | |
| *C07C 251/08* | (2006.01) | |
| *C07C 251/20* | (2006.01) | |
| *C10G 45/48* | (2006.01) | |
| *C10G 45/52* | (2006.01) | |
| *C10G 50/00* | (2006.01) | |
| *C10G 69/12* | (2006.01) | |
| *C08F 10/00* | (2006.01) | |
| *C07F 15/04* | (2006.01) | |
| *B01J 31/22* | (2006.01) | |
| *C07C 251/24* | (2006.01) | |
| *C08F 8/04* | (2006.01) | |
| *C10M 177/00* | (2006.01) | |
| *C10M 107/10* | (2006.01) | |
| *C08F 110/02* | (2006.01) | |
| *C08F 110/08* | (2006.01) | |
| *C10G 50/02* | (2006.01) | |

(52) U.S. Cl.
CPC ........ *C10M 105/04* (2013.01); *B01J 31/1805* (2013.01); *B01J 31/2295* (2013.01); *C07C 251/08* (2013.01); *C07C 251/20* (2013.01); *C07C 251/24* (2013.01); *C07C 323/45* (2013.01); *C07F 15/04* (2013.01); *C07F 15/045* (2013.01); *C08F 8/04* (2013.01); *C08F 10/00* (2013.01); *C08F 110/02* (2013.01); *C08F 110/08* (2013.01); *C10G 45/48* (2013.01); *C10G 45/52* (2013.01); *C10G 50/00* (2013.01); *C10G 50/02* (2013.01); *C10G 69/126* (2013.01); *C10M 107/10* (2013.01); *C10M 177/00* (2013.01); *B01J 2231/20* (2013.01); *B01J 2531/824* (2013.01); *B01J 2531/847* (2013.01); *B01J 2540/225* (2013.01); *B01J 2540/30* (2013.01); *C07C 2603/20* (2017.05); *C07C 2603/26* (2017.05); *C10G 2300/1088* (2013.01); *C10G 2300/302* (2013.01); *C10G 2300/304* (2013.01); *C10G 2400/10* (2013.01); *C10M 2205/028* (2013.01); *C10M 2205/0285* (2013.01); *C10N 2270/00* (2013.01)

(58) Field of Classification Search
CPC ... C07C 251/08; C07C 251/20; C07C 251/24; C10M 105/04
See application file for complete search history.

(56) References Cited

U.S. PATENT DOCUMENTS

| | | | |
|---|---|---|---|
| 4,284,835 A | 8/1981 | Kim et al. | |
| 6,063,973 A | 5/2000 | Sen et al. | |

(Continued)

FOREIGN PATENT DOCUMENTS

| | | |
|---|---|---|
| CA | 1056408 A | 6/1979 |
| CA | 2211108 C | 5/2001 |

(Continued)

OTHER PUBLICATIONS

International Search Report corresponding to Application No. PCT/CN2012/074545 dated Aug. 2, 2012 (5 pages).

(Continued)

*Primary Examiner* — Pancham Bakshi
(74) *Attorney, Agent, or Firm* — Kilpatrick Townsend & Stockton LLP

(57) ABSTRACT

The present invention discloses a catalytic system for preparing highly branched alkane from olefin, which contains novel nickel or palladium complexes. In the presence of the catalytic system, highly branched oily alkane mixture can be efficiently obtained from olefins (such as ethylene) under mild conditions. The alkane mixture has a low bromine number, and can be used as a processing aid(s) and lubricant base oil with high-performance. Provides also was a method for preparing the catalyst and a method for preparing an oily olefin polymer.

10 Claims, 2 Drawing Sheets

(56) References Cited

U.S. PATENT DOCUMENTS

| | | | |
|---|---|---|---|
| 6,103,658 | A | 8/2000 | Mackenzie et al. |
| 6,660,677 | B1 | 12/2003 | Mackenzie et al. |
| 9,315,755 | B2* | 4/2016 | Tang .................. C10G 69/126 |
| 2002/0065192 | A1 | 5/2002 | Mackenzie et al. |
| 2003/0060357 | A1 | 3/2003 | Arndt-Rosenau et al. |
| 2005/0077208 | A1* | 4/2005 | Miller .................. C10M 107/02 208/18 |

FOREIGN PATENT DOCUMENTS

| | | |
|---|---|---|
| CN | 1560092 A | 1/2005 |
| CN | 1884312 A | 12/2006 |
| CN | 101531725 A | 9/2009 |
| CN | 102050840 A | 5/2011 |
| CN | 102093425 A | 6/2011 |
| CN | 102180910 A | 9/2011 |
| CN | 102250152 A | 11/2011 |
| DE | 10 2009 017 827 A1 | 10/2010 |
| EP | 1 284 271 A1 | 2/2003 |
| EP | 1284271 A1 | 2/2003 |
| JP | S59-161495 A | 9/1984 |
| JP | S62-121710 A | 6/1987 |
| JP | 2002-509955 A | 4/2002 |
| JP | 2003-064127 A | 5/2003 |
| JP | 2007-270059 A | 10/2007 |
| JP | 2009-501836 A | 1/2009 |
| JP | 2009-227996 A | 10/2009 |
| JP | 2010-090255 A | 4/2010 |
| WO | 96/23010 A2 | 8/1996 |
| WO | 98/03521 A1 | 1/1998 |
| WO | 98/33823 A1 | 8/1998 |
| WO | 98/40374 A2 | 9/1998 |
| WO | 98/58972 A1 | 12/1998 |
| WO | 99/05189 A1 | 2/1999 |
| WO | 99/20720 A1 | 4/1999 |
| WO | 99/47627 A1 | 9/1999 |
| WO | 99/50320 A2 | 10/1999 |
| WO | 9962968 A1 | 12/1999 |
| WO | 00/06620 A2 | 2/2000 |
| WO | 2004/007509 A1 | 1/2004 |
| WO | 2005/105734 A1 | 11/2005 |
| WO | 2006/083540 A1 | 8/2006 |

OTHER PUBLICATIONS

Johnson, Lynda K. et al., "New PD(II)- and Ni(II)-Based Catalysts for Polymerization of Ethylene and α-Olefins," J. Am. Chem. Soc. (1995), 117:6414-6415.

Kim, Jang Sub et al., Novel Nickel(II)- and Palladium(II)-Based Catalytic Systems for the Synthesis of Hyperbranched Polymers from Ethene, J. Am. Chem. Soc.(1998), 120:1932-1933.

Murtuza, Shahid et al., "Tantalum- and Titanium-Based Catalytic Systems for the Synthesis of Hyperbranched Polyethen," J. Am. Chem. Soc. (2000), 122:1867-1872.

Extended European Search Report corresponding to EP 12785810 dated Sep. 1, 2015 ; 15 pages.

First Office Action corresponding to JP 2014-510649 (non-English); 9 pages (see, p. 9 of Action for list of named references cited herein).

Gasperini, Michela et al., "Synthesis of mixed Ar,Ar'-BIAN ligands (AR,Ar'-BIAN = bis(aryl) acenaphthenequinonediimine). Measure of the coordination strength of hemilabile ligands with respect to their symmetric counterparts," The Royal Society of Chemistry (Sep. 10, 2004); 7 pages.

Jeon, Manseong et al., "Polymerizations of Propylene with Unsymmetrical (α-Diimine)nickel(II) Catalysts," Macromolecular Research (Mar. 2, 2006); 14(3):306-311.

Jeon, Manseong et al., "Ethylene Polymerizations with Unsymmetrical Unsymmetrical (α-Diimine)nickel(II) Catalysts," Polymer Journal (Mar. 12, 2008) 40(5):409-413.

Liu, Hao et al., "2,6-Dibenzhydryl-N-(2-phenyliminoacenaphthylenylidene)-4-methylbenzamine Nickel Dibromides: Synthesis, Characterization, and Ethylene Polymerization," Organometallics (Mar. 22, 2011); 2418-2424.

Schleis, Thomas et al., "Ni(II) and Pd(II) complexes of camphor-derived diazadiene ligands: steric bulk tuning and ethylene polymerization," Inorganic Chemistry Communications (Aug. 3, 1998); 1:431-434.

Schmid, Markus et al., "Novel Non-Symmetric Nickel-Diimine Complexes for the Homopolymerization of Ethene: Control of Branching by Catalyst Design," Z. Naturforsch (Jun. 28, 2002) 57 b:1141-1146.

Szabo, Miklos J. et al., "Copolymerization of Ethylene with Polar Monomers by Anionic Substitution. Theoretical Study Based on Acrylonitrile and the Brookhart Diimine Catalyst," Organmetallics (Mar. 31, 2005); 24:2147-2156.

Viscosity calculator—Viscosity Index: ASTM D2270 / Viscosity Index (VI) downloaded from Web Aug. 19, 2015: http://www.viscopedia.com/calculator/astm-d2270-viscosity-index.

Japanese Office Action corresponding to JP 2016-093507; 9 pages (see, p. 8 of Action for English list of named references cited herein).

\* cited by examiner

CATALYTIC SYSTEM FOR PREPARATION OF HIGH BRANCHED ALKANE FROM OLEFINS

CROSS REFERENCE TO RELATED APPLICATIONS

This application is a continuation of U.S. application Ser. No. 14/118,172, filed Dec. 5, 2013, now allowed, which application is a 371 National Stage Entry of PCT/CN2012/074545, filed Apr. 23, 2012, which claims the benefit of priority of CN 201110126431.9, filed May 16, 2011 and CN 201210098399.2, filed Apr. 5, 2012, the disclosures of which are hereby incorporated by reference in their entireties for all purposes.

TECHNICAL FIELD

The invention relates to the field of catalysis and the field of lubricant base oil, particularly relates to a series of α-diimine nickel or palladium catalysts and the preparation techniques thereof, and a method for preparing highly branched oily alkane from olefin (such as ethylene, propylene, butane) in the presence of this series of catalysts and a use of the highly branched oily alkane.

BACKGROUND ART

Industrial lubricant base oil is a mixture of several branched alkane, obtained by petroleum cracking or α-olefin oligomerization (PAO). Wherein, PAO, as a series of very important and promising lubricant base oil, is produced by α-olefin oligomerization, and the main raw material is expensive α-olefin such as α-octene, α-decene, α-dodecene and the like.

So in order to get high quality base oil PAO, α-olefin (particularly α-decene), must be obtained firstly by ethylene oligomerization with catalysts. It is difficult to produce α-olefin with more than C6 selectively, and it is economical and efficient to produce high quality base oil directly from cheap olefins such as ethylene, propylene, butene and the like. However, there is no significant progress in this area because of lacking efficient catalytic system.

Before 1995, nickel complex was believed to only catalyze oligomerization of olefin, for example the well-known SHOP catalyst could effectively catalyze ethylene to produce a series of α-olefin with Flory distribution. In 1995, through α-diimine nickel complexes, Brookhart et al. (*J. Am. Chem. Soc.* 1995, 117, 6414.) firstly proved that the property of the active center could be controlled by changing the structure of a ligand, thereby obtaining branched polyethylene with high molecular weight by ethylene polymerization catalyzed by nickel complexes. The melting point (Tm) of the polymer is 39° C. to 132° C., lower than common polyethylene resin. Respecting to this technology, Du pont has applied several patents (WO 96/23010, WO 98/03521, WO 98/40374, WO 99/05189, WO 99/62968, WO 00/06620, U.S. Pat. Nos. 6,103,658, 6,660,677) to protect such kind of polymer products. The corresponding palladium system could get highly branched oily polymer, however the activity of this system is relatively low. Besides, it is known that this catalyst results in severe β-H elimination. In the presence of the catalyst, β-H elimination producing carbon-carbon double bond and Pd—H are the main way of such catalytic circle, so the unsaturation is high (the bromine number is high).

The morphology and performance of polyethylene is closely related to the branching degree, and the structure of catalysts is the core to control the structure of polyethylene. The polyethylene produced by Brookhart et al. with nickel catalysts already show a certain degree of branching, but still could not meet the requirement for application of such as lubricant base oil, because the polymer products are solid.

Sen et al. found (*J. Am. Chem. Soc.* 1998, 120, 1932.) that Ni(II), Pd(II)/AlCl$_3$ could catalyze ethylene polymerization to make highly branched oily polyethylene. However, the viscosity index of the oil is relatively low and not suitable for lubricant base oil. They also found (*J. Am. Chem. Soc.* 2000, 122, 1867.) that TaCl$_5$, TiCl$_4$/alkyl aluminium chloride could catalyze ethylene polymerization to make oily polymer, basically without methyl branch. Respecting to this technology, they applied several patents (WO 98/33823, WO 99/47627) to protect the products and the polymerizing method.

Industrial synthetic lubricant needs to meet the requirement of maintaining the viscosity in a large temperature range, which means having a high viscosity index. Also lubricant needs a low pour point, which is to be equal to or lower than the third class oil (group III base oil). BI, the branching degree of the polymer, is connected with these properties of the oil. BI is the ratio of methyl hydrogen number to all alkyl hydrogen number. The methyl hydrogen is characterized as in 0.5-1.05 part of HNMR, and all the alkyl hydrogen is characterized as in 0.5-2.1 part of HNMR. Generally, the pour point of lubricant oil decreases as BI increases, which means the temperature at which the lubricant oil changes from liquid to solid decreases, and the decreasing of the pour point is good for expanding the application of lubricant. However, the increase of BI generally results in the decrease of oil viscosity index, which is unfavorable for the application of lubricant. Therefore, synthetic lubricant aims to ensure the oil remaining in a liquid state under lower temperature, and have a high viscosity index, for example, maintaining a high viscosity at high temperature, such as 100° C.

In summary, there is no promising system to produce highly branched alkane directly from olefin, such as ethylene. Therefore, it is urgent to develop a high-efficient method for preparing highly branched oily polymer directly from low-cost olefin such as ethylene and the corresponding catalytic system.

SUMMARY OF THE INVENTION

The object of the present invention is to provide a novel catalytic system and the preparation of the key catalyst therein. Through regulating the catalyst structure, the catalytic system could prepare highly branched oily polymer directly from low-cost olefins, such as ethylene, propylene or butene.

Another object of the present invention is to provide an application of the novel catalytic system in synthesis of highly branched alkane.

Another object of the present invention is to provide a series of highly branched alkane used for advanced lubricant base oil.

In the first aspect of the present invention, a compound of formula I is provided,

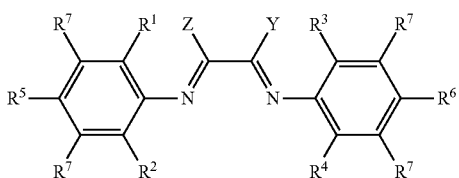

wherein,

Z and Y are independently hydrogen, $C_1$-$C_4$ alkyl or $C_1$-$C_4$ haloalkyl, unsubstituted or substituted phenyl, or Z and Y together with the adjacent carbon atom form an unsubstituted or substituted group selected from the following group: acenaphthyl, phenanthryl, and $C_5$-$C_8$ cycloalkyl, wherein the substituted phenyl, acenaphthyl, phenanthryl or cycloalkyl has 1 to 5 substituents selected from the group: halogen, $C_1$-$C_4$ alkyl and $C_1$-$C_4$ haloalkyl;

$R^1$, $R^2$, $R^3$ and $R^4$ are independently H, halogen, $C_1$-$C_8$ alkyl, $C_1$-$C_8$ haloalkyl, unsubstituted or substituted phenyl, —O—$R_a$, —$CH_2$—O—$R_a$, —$SR_b$ or —$CH_2$—S—$R_b$, where $R_a$ and $R_b$ are independently $C_1$-$C_8$ alkyl, unsubstituted or substituted phenyl, and provide that of $R^1$, $R^2$, $R^3$ and $R^4$, $R^1 \neq R^3$ and/or $R^2 \neq R^4$; the substituted phenyl has 1 to 5 substituents selected from the group: halogen, $C_1$-$C_4$ alkyl and $C_1$-$C_4$ haloalkyl;

$R^5$, $R^6$ and $R^7$ are independently halogen, nitro, hydrogen, $C_1$-$C_8$ alkyl, $C_1$-$C_8$ haloalkyl, —O—$R_a$, —$CH_2$—O—$R_a$, or —N($R_c$)$_2$, wherein $R_a$ is $C_1$-$C_8$ alkyl, unsubstituted or substituted phenyl, and Rc is $C_1$-$C_4$ alkyl or haloalkyl; the substituted phenyl has 1 to 5 substituents selected from the following: halogen, $C_1$-$C_4$ alkyl and $C_1$-$C_4$ haloalkyl.

In another preferred embodiment, 1 to 3 substituent(s) of $R^1$, $R^2$, $R^3$ and $R^4$ are $C_1$-$C_8$ alkyl, $C_1$-$C_8$ haloalkyl or unsubstituted or substituted phenyl, and 1 to 3 of substituent(s) are hydrogen or halogen.

In another preferred embodiment, the substituted phenyl has 1-3 substituents.

In another preferred embodiment, Z and Y together with the adjacent carbon atom form an unsubstituted or substituted acenaphthylene group.

In another preferred embodiment, $R^1$ and $R^2$ are selected from the following group: H, methyl, halogen, or —$CH_2$—O—$R_a$.

In another preferred embodiment, $R^1$ and $R^2$ are selected from the following group: phenyl, benzyl, halogen, or —$CH_2$—O—$R_a$.

In another preferred embodiment, $R^1$ and $R^2$ are selected from the following group: —$SR_b$, or —$CH_2$—S—$R_b$.

In the second aspect of the present invention, a complex is provided, which is formed by the compound of the first aspect of the present invention and a salt(s) of divalent metal selected from the following group: nickel, palladium or the combination thereof.

In another preferred embodiment, the complex is shown as formula II:

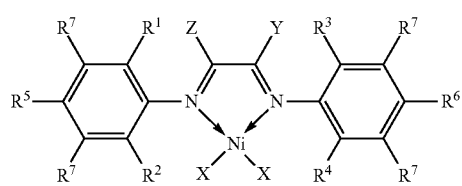

wherein,

Z, Y, $R^1$, $R^2$, $R^3$, $R^4$, $R^5$, $R^6$ and $R^7$ are defined as above;

X is halogen, $C_1$-$C_4$ alkyl, $C_2$-$C_6$ alkenyl, allyl or benzyl.

In another preferred embodiment, X is chloride, bromine, iodine, methyl, allyl or benzyl.

In another preferred embodiment, X is chloride, bromine or iodine.

In the third aspect of the present invention, it is provided that a process for preparing the complex of the second aspect of the present invention, comprising a step of:

In inert solvent, reacting the compound of the first aspect of the present invention with a divalent metal salt(s), thereby forming a complex of the second aspect, wherein the metal precursor is a divalent nickel compound or a divalent palladium compound.

In another preferred embodiment, the metal precursor includes: $NiCl_2$, $NiBr_2$, $NiI_2$, (DME)$NiBr_2$, $PdCl_2$, $PdBr_2$, Pd(OTf)$_2$, Pd(OAc)$_2$ or the combination thereof.

In another preferred embodiment, the reaction is conducted in basically anhydrous conditions (e.g., water content ≤0.1%).

In another preferred embodiment, the reaction is conducted under inert atmosphere (e.g. nitrogen)

In the fourth aspect of the present invention, it is provided a process for preparing the compound of formula I, comprising steps of:

(a) reacting Diketone of formula A with amine compounds of formula B, forming compounds of formula C;

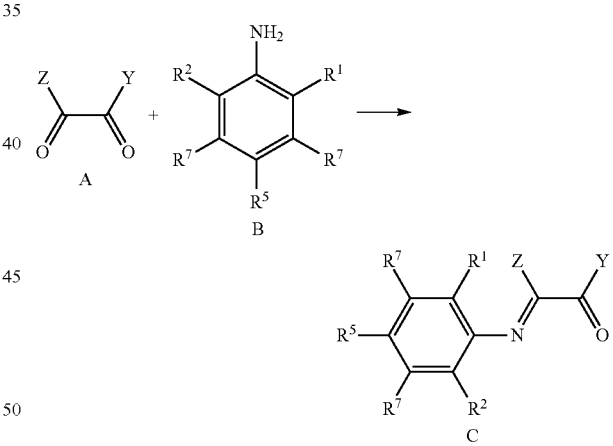

(b) Reacting Compounds of formula C with amine compounds of formula D, forming compounds of formula I;

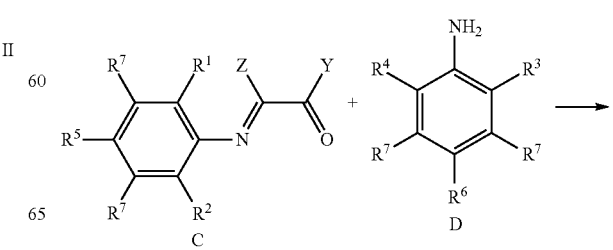

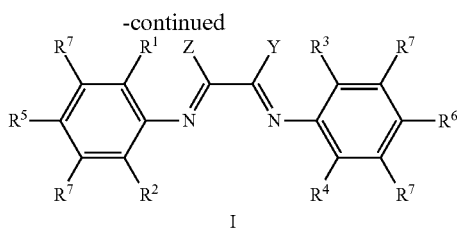

wherein, Z, Y, $R^1$, $R^2$, $R^3$, $R^4$, $R^5$, $R^6$ and $R^7$ are defined as above.

In another preferred embodiment, the step (a) or step (b) is conducted in inert solvent, and heated separately for 1-96 hours (preferably 2 to 72 hours).

In another preferred embodiment, in step (a) or step (b), 0.001 to 100% of a appropriate catalyst(s) promoting the condensation reaction is added, wherein, preferably the catalyst is acetic acid, p-toluenesulfonic acid, $TiCl_4$, or orthosilicate.

In another preferred embodiment, in step (a), the ratio of compound A and B is (0.7-1.2):1.

In another preferred embodiment, in step (b), the ratio of compound C and D is (0.7-1.2):1.

In another preferred embodiment, in step (a) or step (b), the inert solvent includes: alcohols, aromatic hydrocarbons, aliphatic hydrocarbons, halogenated hydrocarbons, ethers, esters.

In another preferred embodiment, in step (a) and step (b), the inert solvent is methanol, ethanol, toluene, xylene or mesitylene.

In the fifth aspect of the present invention, it is provided that a process for preparing oily polyolefin, comprising a step of:

(a) in the presence of the complex of the second aspect of the invention as a catalyst for olefin polymerization, polymerizing olefin, thereby forming oily polyolefin.

In another preferred embodiment, the olefin is unsubstituted $C_2$-$C_{10}$ alkene, substituted $C_2$-$C_{10}$ alkene or the combination thereof.

In another preferred embodiment, the olefin is ethylene, propylene, butylene or the combination thereof.

In another preferred embodiment, the olefin is any combination of ethylene, propylene and/or butene with a $C_5$-$C_{12}$ olefin(s).

In another preferred embodiment, the olefin is ethylene.

In another preferred embodiment, the oily polyethylene is highly branched; preferably, there is 100-500 methyl per 1000 methylene ($CH_2$) in the highly branched polyethylene.

In another preferred embodiment, there is also a cocatalyst in step (a).

More preferably, the cocatalyst is selected from the following group or their combination: alkyl aluminum reagents (such as alkyl aluminoxanes, diethylaluminum chloride and ethyl aluminum dichloride).

In another preferred embodiment, in step (a), the reaction temperature is 0-100° C.

In another preferred embodiment, in step (a), the reaction condition is: the pressure (gauge pressure) is 0.1-3 MPa, the cocatalyst is alkyl aluminoxane or diethyl aluminum chloride, wherein the molar ratio of aluminum in cocatalyst and nickel in catalyst is 10-5000.

In another preferred embodiment, step (a) is conducted in a polymerization solvent which is selected from the following group: toluene, n-hexane, dichloromethane, 1,2-dichloroethane, chlorobenzene, tetrahydrofuran, or the combination thereof.

In another preferred embodiment, step (a) could be conducted in oily polyethylene or an oily alkane mixture.

In another preferred embodiment, the process further comprises a step of:

(b) Hydrogenating the oily polyolefin obtained in step (a), thereby obtaining a hydrogenated oily alkane mixture.

In another preferred embodiment, the oily alkane mixture has the following features:

(i) there is 100-500 methyl per 1000 methylene in the polymer chain.

(ii) the bromine number is less than 0.5 g/100 g.

(iii) the molecular weight is 300-500,000 g/mol.

In another preferred embodiment, a following step is further comprised between step (a) and step (b): separating the oily polyolefin.

In another preferred embodiment, in step (a), hydrogenation reaction is conducted simultaneously.

In another preferred embodiment, step (b) could be carried out in inert solvent or directly be carried out in polyolefin oil as solvent.

In the sixth aspect of the present invention, it is provided that an oily olefin polymer, possessing the following characteristics: there is 100-500 methyl per 1000 methylene, and the molecular weight is 300-500,000 g/mol.

In another preferred embodiment, the oily polymer is prepared by the method of the fifth aspect of the present invention.

In another preferred embodiment, the oily polymer is oily polyethylene.

In the seventh aspect of the present invention, an oily alkane mixture is provided, possessing the following characteristic: there is 100-500 methyl per 1000 methylene and the bromine number is less than 0.5 g/100 g.

In another preferred embodiment, the oily alkane mixture is a hydrogenation product of the oily olefin polymer of the sixth aspect of the invention.

In another preferred embodiment, the oily alkane mixture is a hydrogenation product of oily polyethylene.

In another preferred embodiment, the oily alkane mixture is prepared by the following method:

(b) Hydrogenating the polyolefin obtained in step (a), thereby obtaining a hydrogenated oily alkane mixture.

In another preferred embodiment, the oily alkane mixture has the following characteristic:

(i) there is 100-500 methyl per 1000 methylene in the polymer chain.

(ii) the bromine number is less than 0.5 g/100 g. and (iii) the molecular weight is 300-500,000 g/mol.

In another preferred embodiment, a following step is further comprised between step (a) and step (b): separating the oily polyethylene.

In another preferred embodiment, in step (a), hydrogenation reaction is conducted simultaneously.

In another preferred embodiment, step (b) is carried out in inert solvent or directly be carried out in polyolefin oil as solvent.

In the eighth aspect of the present invention, it is provided that a use of the oily alkane mixture of the seventh aspect of the invention as lubricant base oil, a lubricant additive(s), a plasticizer(s) or a processing aid(s) of resin.

In the ninth aspect of the present invention, a lubricant is provided, comprising the oil alkane mixture of the seventh aspect of the invention.

In another preferred embodiment, the lubricant contains 0.1-100 wt % (preferably 1-90 wt %) of the oily alkane mixture.

In the tenth aspect of the present invention, it is provided that a use of the complex of the second aspect of the invention as a catalyst for olefin polymerization.

In another preferred embodiment, the olefin polymerization is carried out under homogeneous condition.

In another preferred embodiment, the catalyst is loaded on an inorganic carrier or an organic carrier.

In the eleventh aspect of the present invention, an oily alkane mixture is provided, having the following characteristic:

(a) the viscosity index is 100-300.
(b) the pour point is −50° C. to −10° C.
(c) the molecular weight is 300 to 500,000 g/mol; and
(d) there is 100-500 methyl per 1000 methylene.

In another preferred embodiment, the oily alkane mixture has the following characteristic:

(e) the branching degree BI is ≥0.20; and/or
(f) the bromine number is ≤0.5 g/100 g.

In another preferred embodiment, the viscosity index of the oily alkane mixture is 150-300, more preferably 180-300, most preferably 200-290.

In another preferred embodiment, the branching degree is 0.22~0.50, preferably 0.22~0.45, more preferably 0.24~0.40.

In another preferred embodiment, the molecular weight of the oily alkane mixture is 500 to 500,000 g/mol, more preferably 800 to 200,000 g/mol, 1000 to 100,000 g/mol.

In the twelfth aspect of the present invention, it is provided a method for preparing the oily alkane mixture of the eleventh aspect of the invention, comprising steps of: hydrogenating the oily polyolefin to form the oily alkane mixture, and the oily polyolefin has the following features: there is 100-500 methyl per 1000 methylene and the molecular weight is 300 to 500,000 g/mol.

In another preferred embodiment, of the oily olefin polymer (i.e. the oily polyolefin), there is about 100 to 500 alkyl branched chains per 1000 methylene, and per each 100 methyl branched chain there is 20-100 ethyl branched chains, 2-50 propyl branched chains, 20-100 butyl branched chains, 2-50 pentyl branched chains and 20-200 hexyl or longer branched chains.

More preferably, there is about 150 to 300 alkyl branched chains per 1000 methylene, and per each 100 methyl branched chains there is about 50-100 ethyl branched chains, about 5-20 propyl branched chains, about 30-80 butyl branched chains, about 5-20 pentyl branched chains and about 50-100 hexyl or longer branched chains.

In the thirteenth aspect of the present invention, it is provides a use of the oily alkane mixture of the eleventh aspect of the invention, selected from the following group:

(a) for preparing a lubricant;
(b) as a lubricant additive(s) or lubricant base oil;
(c) as a processing aid(s) of resin; or
(d) as a plasticizer(s).

In the fourteenth aspect of the present invention, a lubricant is provided, comprising base oil and an additive(s), and the base oil is the oily alkane mixture of the eleventh aspect of the invention.

In another preferred embodiment, the additive(s) is selected from: a viscosity index improver(s), a pour point depressant(s), an antioxidant(s), a detergent(s), a friction moderator(s), an oiliness agent(s), a extreme pressure agent(s), an anti-foam agent(s), a metal deactivator agent(s), a emulsifying agent(s), a corrosion inhibitor(s), a rust inhibitor(s), a demulsifier(s), an antioxidative corrosion inhibitor(s) or the combination thereof.

In the fifteenth aspect of the present invention, it is provides a method for preparing a lubricant, comprising the step of mixing the oily alkane mixture of the eleventh aspect of the invention evenly with an additive(s), thereby obtaining the lubricant.

In another preferred embodiment, the additive(s) is selected from: a viscosity index improver(s), a pour point depressant(s), an antioxidant(s), a detergent(s), a friction moderator(s), an oiliness agent(s), a extreme pressure agent(s), an anti-foam agent(s), a metal deactivator agent(s), a emulsifying agent(s), a corrosion inhibitor(s), a rust inhibitor(s), a demulsifier(s), an anti corrosion agent(s) or the combination thereof.

It should be understood that in the scope of the invention, the technical features of the invention described above and the technical features specifically described below (example) may be combined with each other, and thus constitute a new or preferred technical solution. Due to space limitations, this is no longer described.

DESCRIPTION OF FIGURES OF THE INVENTION

DETAILED DESCRIPTION OF THE INVENTION

Figure 1:
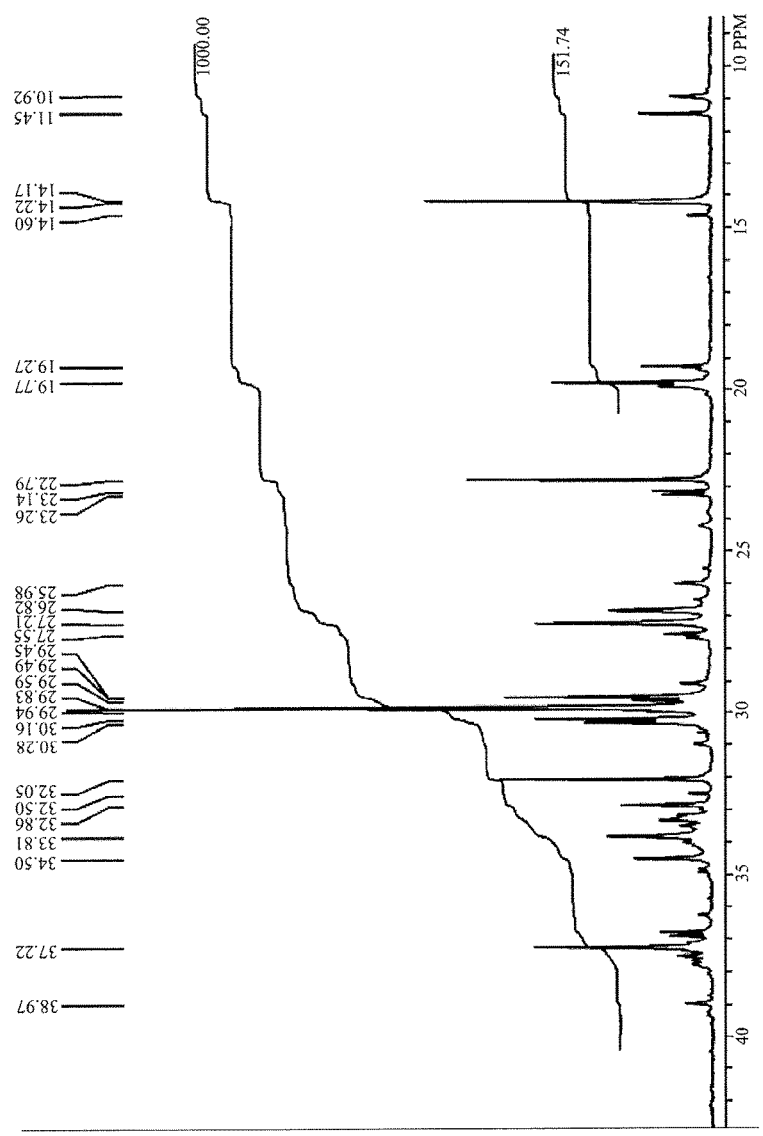
FIG. 1 shows the $^{13}$CNMR of the polymer prepared in one example of the present invention.

After extensive and deeply studies, the present inventors have prepared a novel ligand compound, a complex and a catalytic system by changing the structure of the catalyst, thus highly branched oily polymer is firstly obtained by polymerizing ethylene directly with high catalytic activity. Through the adjustment of the catalyst structure, the catalytic system could polymerize propylene or butylene directly with high catalytic activity to obtain highly branched oily polymer. The oily polymer of the present invention could be used to prepare high branched alkanes with excellent performance, thus significantly reducing the cost of promising lubricant. On this basis, the present invention is completed.

Term

As used herein, "group I base oil" refers to the base oil of which the process is basically dominated by the physical process without changing the structure of the hydrocarbon. The quality of group I base oil is greatly effected by the raw material, and thus the performance is limited.

As used herein, "group II base oil" refers to the base oil obtained by a combined process (a combination of a solvent process and a hydrogenation process). Although their performance such as thermal stability improves, the viscosity index and the pour point and other properties are not yet satisfactory.

As used herein, "group III base oil" means the base oil obtained by hydrogenation process. Although the Group III base oil has advantages such as a low volatility, etc., some properties like the viscosity index and the pour point, etc. could not satisfy some specific application.

As used herein, "olefin" means polymerizable compounds containing "C=C" bond. Representative olefin includes substituted or unsubstituted $C_2$-$C_{10}$ olefin, preferably $C_2$-$C_6$ olefin, such as ethylene, propylene, butene and so on. The substituent(s) is not particularly limited in species and number. Usually a monomer may contain 1-5 substituent(s). Representative substituents include (but are not limited to)

hydroxyl, ester group, silylane group, amino (substituted amino), cyano, halogen, carbonyl of ketone, heterocyclic group, carboxyl, trifluoromethyl. Representative substituted olefin is a polar monomer containing various functional groups that still could be polymerized.

Ligand

The present invention provides a ligand compound of formula I.

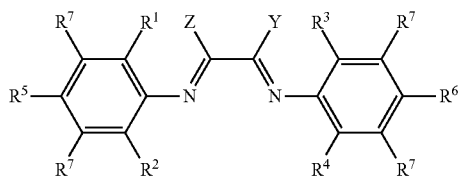

wherein, each group is defined as above.

The functional substituents of hydrocarbyl groups may be present in the Z, Y, $R^1$, $R^2$, $R^3$, $R^4$, $R^5$, $R^6$ and $R^7$ include: hydroxyl, ether group, ester group, dialkylamino, carboxyl, oxo (aldehyde and ketone), nitro group, amide, thioether, preferably, hydroxyl, ether group, dialkyl amine.

Preferably, Z and Y are independently methyl, phenyl, or phenyl substituted by alkyl, halogen, alkoxyl; the halogen include: fluorine, chlorine, bromine or iodine; the alkoxyl is preferably methoxyl, ethoxyl, isopropoxyl; the alkyl-substituted phenyl is preferably $C_1$-$C_6$ alkyl-substituted phenyl, more preferably $C_1$-$C_4$ alkyl-substituted phenyl, most preferably methyl, ethyl, isopropyl or butyl-substituted phenyl. The substituents could be in any position of the phenyl ring.

Preferably, Z and Y together with the adjacent carbon atom form acenaphthenyl

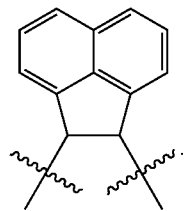 [SMILES: *C1c2cccc3cccc(c23)C1*]

Preferably, Z and Y together with the adjacent carbon atom form cyclohexyl.

Preferably, $R^1$, $R^2$ is $C_1$-$C_8$ alkyl or substituted $C_1$-$C_8$ alkyl, and $R^3$, $R^4$ is hydrogen, halogen or CF3; provided that $R^1$, $R^2$ and $R^3$, $R^4$ are not identical;

Preferably, $R^1$, $R^2$ is $C_1$-$C_8$ alkyl or substituted $C_1$-$C_5$ alkyl, and $R^3$ is hydrogen, halogen or CF3, and $R^4$ is substituted $C_1$-$C_8$ alkyl.

Preferably, $R^1$, $R^2$ is $C_1$-$C_4$ alkyl or substituted $C_1$-$C_4$ alkyl, and $R^3$ is halogen or CF3, and $R^4$ is halogen.

In another preferred embodiment, $R^1$ and $R^2$ are H, methyl, halogen, —$CH_2$—O—$R_a$ or —O—$R_a$.

In another preferred embodiment, $R^1$ and $R^2$ are phenyl, benzyl, halogen, —$CH_2$—O—$R_a$ or —O—$R_a$.

In another preferred embodiment, $R^1$ and $R^2$ are selected from the group: —$SR_b$ or —$CH_2$—S—$R_b$.

Preferably, $R^5$, $R^6$, $R^7$ is hydrogen, $C_1$-$C_8$ alkyl, substituted $C_1$-$C_8$ alkyl, halogen, nitro, methoxyl, dimethylamino, trifluoromethyl;

The substituted alkyl is preferably alkyl substituted by halogen, alkoxy, phenoxy; wherein halogen includes fluorine, chlorine, bromine or iodine; the alkoxyl is preferably methoxyl, ethoxyl, isopropoxyl, more preferably methoxyl.

The structure of the preferred ligand includes:

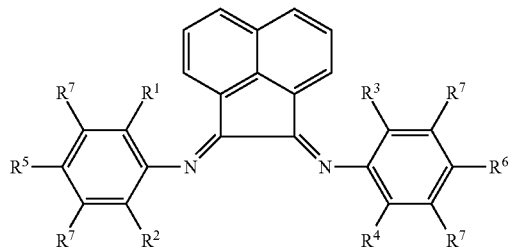

IA

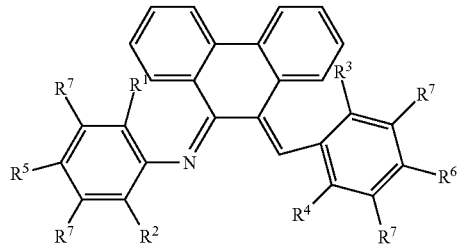

IB

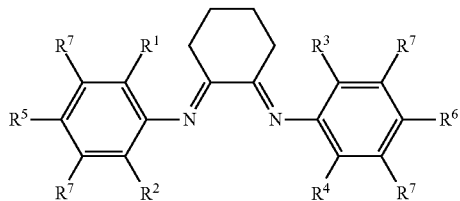

IC

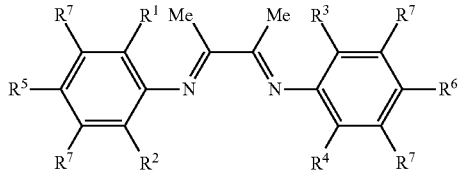

ID

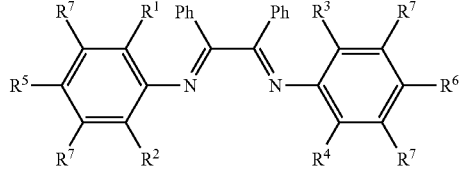

IE

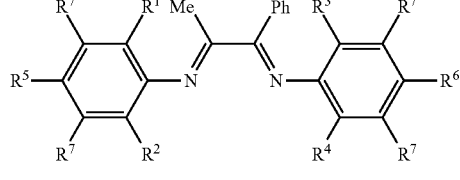

IF wherein, each group is defined as above.

Complex

In the present invention, compounds of formula I could react with divalent nickel or palladium salts to form the corresponding nickel or palladium complex.

In the present invention, the complex of formula II is preferred:

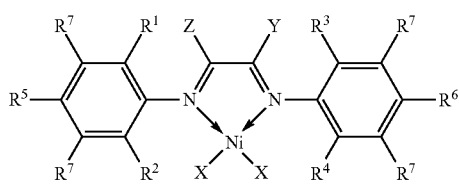

wherein, each group is defined as above.

X may be halogen, $C_1$-$C_4$ alkyl, $C_2$-$C_6$ alkenyl, allyl, benzyl; wherein the $C_1$-$C_4$ alkyl is preferably methyl; the halogen is preferably bromine, chlorine or iodine.

In another preferred embodiment, X is chlorine, bromine, iodine, methyl, allyl or benzyl.

In another preferred embodiment, X is chlorine, bromine or iodine.

In the present invention, the ligand compound of the present invention could react with a divalent metal precursor, thereby forming the corresponding complex.

In the present invention, the divalent metal precursor include: $NiCl_2$, $NiBr_2$, $NiI_2$, $(DME)NiBr_2$, $(DME)NiCl_2$, $(DME)NiI_2$, $PdCl_2$, $PdBr_2$, $Pd(OTf)_2$ and $Pd(OAc)_2$.

The metal complex of the present invention could catalyze ethylene polymerization to produce oily polymer in the presence of a cocatalyst(s).

Preparation of Ligand Compounds and Complexes

The present invention also provides the synthesis of the ligand compounds of formula I, comprising the steps of:

(a) reacting diketone A with amine compound B to obtain compound C.

(b) reacting compound C with amine compound D to obtain ligand I.

The compound A, B, C, or D is shown as below:

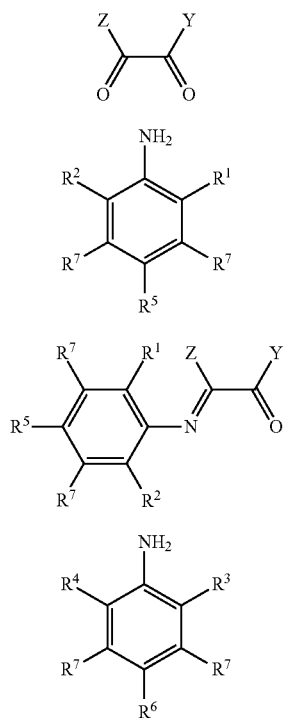

0.001 to 100% of a corresponding catalyst is needed to promote the condensation reaction, such as acetic acid, p-toluenesulfonic acid, TiCl4, orthosilicate ester. Particularly, dikeone A was mixed with amine B in inert solvent to form single imine C under the activation of a catalyst(s) such as 0.001-100% of acetic acid. Compound C reacts with amine D to form product of formula (I). The inert solvent used in the condensation reaction includes alcohols, aromatic hydrocarbons, aliphatic hydrocarbons, halogentated hydrocarbons, ethers, and esters; preferably the alcohols, such as methanol, ethanol; the aromatic hydrocarbon can also show excellent results, such as toluene, xylene, mesitylene and so on. To obtain good results, different substituents should be selected on amine B and D, particularly, on $R^1$, $R^2$ and $R^3$, $R^4$, but the substituents at 2-position and 6-position of the same amine may be identical or different.

Preferably, step (a) or step (b) is respectively heated for 1-96 hours in inert solvent.

Preferably, in step (a) or step (b), 0.001-100% of a catalyst(s) to promote the condensation reaction is added, preferably, acetic acid, p-toluenesulfonic acid, TiCl4, orthosilicate.

Preferably, in step (a), the ratio of compound A and B is (0.7-1.2):1.

Preferably, in step (b), the ratio of compound C and D is (0.7-1.2):1.

Preferably, the inert solvent of step (a) or step (b) is alcohols, aromatic hydrocarbons, aliphatic hydrocarbons, halogenated hydrocarbons, ethers, esters.

Preferably, the inert solvent of step (a) or step (b) is methanol, ethanol, toluene, xylene or mesitylene.

Compound C obtained in step (a) is used in step (b) with or without separation and purification.

The invention also provides a method for preparing complexes. For example, nickel complexes could be synthesized by compound I and metal precursors (including $NiCl_2$, $NiBr_2$, $NiI_2$ or $(DME)NiBr_2$, $(DME)NiCl_2$, $(DME)NiI_2$) under an anhydrous and anaerobic condition and in inert solvent. The inert solvent used may be any conventional solvent which does not affect the reaction, including alcohols, aromatic hydrocarbons, aliphatic hydrocarbons, halogenated hydrocarbons, ethers, esters, and nitriles, preferably halogenated hydrocarbons. Better results could be obtained in solvent of halogenated hydrocarbon and esters, preferred examples are methylene chloride, 1,2-dichloroethane, ethyl acetate, tetrahydrofuran.

$R^1$-$R^7$, X is defined as above. DME refers to ethylene glycol dimethyl ether; complex II (when X is a hydrocarbon group, for example methyl or benzyl) usually could be prepared from the corresponding chloride or bromide II with methyl Grignard reagent or benzyl Grignard reagent under the conventional conditions of the similar reaction. No matter what is X (X is halogen, hydrocarbon group or any other group that can coordination with nickel, such as nitrogen-containing compound, oxygen-containing compound), as long as Ni—C bond or Ni—H bond could be formed in the presence of alkyl aluminum, the catalysis is realized. These compounds have the same active site in catalyzing ethylene polymerization, and thus exhibit the same or similar properties.

Catalytic Systems and the Applications

The present invention provides a catalytic system for olefin (such as ethylene) polymerization to obtain highly branched alkane mixture, the catalytic system comprises 1) the complexes formed by nickel or palladium metal precursor with ligand of formula I; 2) hydrogenation system.

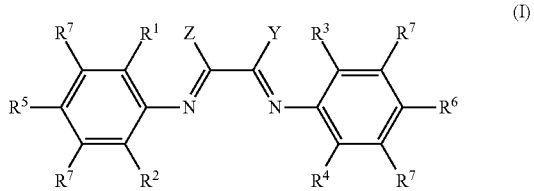

(I)

wherein, each group is defined as above.

Highly branched alkanes could be prepared directly from low-cost olefins (such as ethylene, propylene, butane) in the presense of a catalytic system constituted of the above catalytic system and hydrogenation catalyst. The highly branched alkanes mean aliphatic hydrocarbons having the following characteristic: there is 100-500 methyl per 1000 methylene in the polymer chain, and the bromine number is less than 0.5 g/100 g. Typically, the method includes the following two steps:

1) under the co-action of the above-mentioned metal complexes and cocatalyst, preparing highly branched oily polyolefin (such as polyethylene) directly from olefin (such as ethylene).

2) Hydrogenating the oily polyolefin (such as polyethylene) obtained in step (1) to obtain the hydrogenated oily alkane mixture.

The metal complex is that coordinated by compounds of formula I and divalent nickel or palladium, preferably, is nickel complexes of formula II.

The co-catalyst is reagents that can promote the catalytic reaction, and may be alkyl aluminum compounds or organic boron reagents.

The alkyl aluminum compound comprises any carbon-aluminum bond-containing compounds, including methylaluminoxane (MAO), modified methylaluminoxane (MMAO), triethylaluminum, triisobutylaluminum, diethyl aluminum chloride, ethyl aluminum dichloride and so on. Wherein the ratio of aluminum in co-catalyst and nickel or palladium in catalyst is 10 to 5000; methyl aluminoxane or alkyl aluminum reagents herein may be implemented as co-catalyst to help nickel or palladium complex in catalyzing olefin polymerization to obtain oily polyolefin, and the structure of methyl aluminoxane or alkyl aluminum reagents would not affect the co-catalysis effect, except that the branching degree and the molecular weight of the obtained polymer would be different, due to the structure of co-catalyst, wherein methyaluminoxane, diethyl aluminum chloride, and ethyl aluminum dichloride could obtain the best results.

In another case, desired results could be obtained with the co-catalysis by AlCl3 alone or together with alkyl aluminum compounds.

The highly branched polyolefin (such as polyethylene) of the present invention can be hydrogenated to form highly branched alkanes.

The structure of the highly branched polyolefin (such as polyethylene) is determined by $^{13}CNMR$ and comparison of molecular weight measured by HT-GPC and the actual molecular weight measured by laser light scattering. For example, the molecular weight of polymer obtained in example 41 is 4,570 g/mol measured by GPC, and the molecular weight measured by laser light scattering is 46,400 g/mol, which proved the spherical structure of the highly branched polyethylene.

The highly branched alkane is clear and transparent oil with molecular weight of 500-500,000 g/mol. The highly branched alkane means that the alkane has a spherical or dendritic structure, i.e. has a structure of $R^8R^9CH(CH_2)_nCHR^{10}R^{11}$ or $R^8R^9R^{10}C(CH_2)_nCR^{11}R^{12}$, wherein $R^8$-$R^{12}$ has a structure of $R^{13}R^{14}CH(CH_2)_mCHR^{15}R^{16}$ or $R^{13}R^{14}R^{15}C(CH_2)_nCR^{15}R^{16}R^{17}$; $R^{13}$-$R^{17}$ has a structure of $R^{18}R^{19}CH(CH_2)_xCHR^{20}R^{21}$ or $R^{18}R^{19}R^{20}C(CH_2)_xCR^{20}R^{21}R^{22}$; $R^{18}$, $R^{19}$, $R^{20}$, $R^{21}$, $R^{22}$ is hydrogen, straight-chain or branched-chain alkanes; n, m and x is independently a integer of 1 to 500, preferably, a integer of 1 to 300, more preferably, a integer of 1 to 100.

Take ethylene for example, depending on the specific requirements, in step (1), the contacting time of ethylene and nickel or palladium complexes and alkyl aluminum compounds in inert solvent can be 0.5 to 72 hours, the reacting temperature range is 0-100 degrees, the pressure (means gauge pressure) range is 0.1-3 MPa (1-30 atm).

In step (2), the highly branched oily polyethylene obtained in step (1) was reacted with reduction agents, or in the presence of one or more reduction catalyst, contact the oily polyolefin with hydrogen to obtain highly branched oily alkane mixture with the bromine number less than 0.5 g/100 g. The reduction catalyst can be any catalyst for promoting the hydrogenation process, preferably, hydrogenation catalysts selected from Pd/C, Pd(OH)2, PtO2, rhodium, nickel, ruthenium and so on. The reduction reagents can be any agent that can reduce a double bond, mainly are borane compound, triethyl silane and so on.

In another preferred embodiment, between step (1) and step (2) further comprised is a step of separating oily polyethylene.

In another preferred embodiment, in step (1), hydrogenation reaction is simultaneously conducted.

In another preferred embodiment, the step (2) may be carried out in inert solvent or directly be carried out in the oily polyethylene as solvent; the step (1) may be carried out in inert solvent or be carried out in oily polyethylene as solvent.

Particularly, the step (2) can also complete by the following ways of: a) in step (1), highly branched oily alkane is directly obtained by purging hydrogen simultaneously; b) after step (1), the polymerizing system, without processing, is purged with hydrogen, thereby obtaining highly branched oily alkane; c) after step (1), the polymerizing system, without processing, is added with one or more reducing catalyst for hydrogenation, thereby giving highly branched oily alkane; d) after step (1), separating the oily polyethylene and conducting the hydrogenation reaction.

The above reaction can be conducted in inert solvent, preferably alcohols, alkanes, aromatic hydrocarbons and halogenated hydrocarbons. In step (1), saturated $C_5$-$C_{12}$ hydrocarbon is preferred, such as hexane, heptane; halogenated hydrocarbons (such as dichloromethane, 1,2-dichloroethane, 1,1,2,2-tetrachloroethane), aromatic hydrocarbons (such as toluene, xylene). In step (2), saturated $C_5$-$C_{12}$ hydrocarbons are preferred, such as hexane, heptane, halogenated hydrocarbons (such as dichloromethane, 1,2-dichloroethane, 1,1,2,2-tetrachloroethane), aromatic hydrocarbons (such as toluene, xylene).

In addition to ethylene, by adjusting the structure of catalysts' substituents, the catalytic system can efficiently catalyze propylene or butylene polymerization to form oily polymer, or contact with any combination of ethylene, propylene or butylenes to achieve the catalytic reaction and to obtain oily polymer. When the ethylene, propylene or butene system contains some other $C_5$-$C_{12}$ olefins (such as hexane, octene), it would not affect the catalytic polymerization, and the resulting polymer remains oily, which is highly branched, and is a dendritic or spherical polymer. The polymer can also be hydrogenated in step (2) to obtain highly branched alkane. In another preferred embodiment, between the step (1) and step (2) further comprised is a step of separating the oily polyethylene. The above-mentioned operation of directly obtaining highly branched alkane from ethylene can also be used for these olefins, i.e. in another preferred embodiment, in step (1), hydrogenation reaction is simultaneously conducted; in another preferred embodiment, step (2) can be carried out in inert solvent or can be carried out in oily polyolefin as solvent; step (1) may be carried out in inert solvent or in oily polyolefin as solvent.

In addition to ethylene, the other olefin used in the present invention may be with a double bond at the end or internal olefins, which would not affect the catalytic effect. The internal olefins mean the double bond is at any position other than the end. In the application, the internal olefin can be a mixture of various isomers or a single internal olefin. For example, as for butene, it can be 1-C4, 2-C4, and 2-C4 have cis-isomer and trans-isomer. As being used, it is not limited to 1-C4 or cis-2-C4 or trans-2-C4, and it also can be a mixture of one or more isomer(s), which would not affect the polymerization.

Oily Polyolefin and Oily Alkane Mixture

Catalysts disclosed in the present invention can be applied to the industrially current-used process equipment, for polymerizing all kind of ethylene, propylene and butane, and common reduction process equipment. Both of homogeneous conditions and non-homogeneous conditions with catalyst loaded on organic or inorganic carriers can be used.

The present invention also provides an oily ethylene polymer and the preparation thereof. The oily polyethylene of the invention is highly branched; which means in polyethylene there is 100-500 methyl per 1000 methylene ($CH_2$).

In the present invention, a representative preparation method comprises steps of:

(a) at 0-100° C., under a pressure (gauge pressure) of 0.1-3 MPa (1-30 atm), catalyzing ethylene polymerization with complexes of the present invention as olefin polymerization catalyst, to form oily polyethylene.

Preferably, this step further comprises a co-catalyst; preferably, the co-catalyst is selected from the group: alkyl aluminums (such as alkyl aluminoxane, diethyl aluminum chloride and ethyl aluminum dichloride); wherein the molar ratio of aluminum in co-catalyst and nickel in catalyst is 10 to 5000.

In another preferred embodiment, step (a) is conducted in the solvent selected from: toluene, n-hexane, dichloromethane, 1,2-dichloroethane, cholorobenzene, tetrahydrofuran or the combination thereof.

In a preferred embodiment, the co-catalyst may be alkyl aluminoxane MAO (or modified alkyl aluminoxane MMAO), alkyl aluminum or organic boron reagents, wherein the molar ratio of cocatalyst and nickel or palladium in catalyst is 1-5000.

Since such nickel or palladium complexes have the following characteristic in the reaction process: 1) quick β-H elimination occurs to generate the double bond-containing polyolefin and Ni(Pd)—H bond-containing active species; 2) Ni(Pd)—H bond-containing active species coordinate with α-olefin and insert to obtain the Ni(Pd)—C bond; 3) the obtained Ni(Pd)—C bonds react with ethylene in the system to restart the polymerization; 4) finally terminate the catalytic cycle reaction via β-H elimination. Therefore, the resulting polymer contains a lot of branched-chains, and the number of branched-chains is determined by the signal (integral area) of $CH_2$ and $CH_3$ in $^{13}$CNMR quantitatively.

As the catalytic cycle is terminated by metal's β-H elimination, double bonds are inevitably contained in the polymer chain, and the resulting oily polyolefin is highly unsaturated. For example, in one preferred embodiment, the bromine number of the resulting oily polymer obtained by nickel catalyst-catalyzed ethylene polymerization is 38 g/100 g.

In a typical method of the present invention, in step (a), at 0-100° C., under the pressure (gauge pressure) of 0.1-3 MPa (1-30 atm), catalyzing the polymerization of propylene, butylene or any combination of ethylene, propylene, butylene and other $C_5$-$C_{12}$ olefin in the presence of complexes of the present invention as olefin polymerization catalyst, therefore forming oily polyolefin.

The present invention also provides a highly branched oily alkane mixture. The mixture is the hydrogenated product of the oily polyolefin, wherein the oily polyolefin comprises oily polyethylene, oily polypropylene, oily polybutene or oily polymer obtained from a mixture of the above-mentioned gases with a catalyst. The molecular weight of the oily alkane mixture of the present invention is 500-500,000 g/mol, and there is 100-500 methyl per 1000 methylene. The highly branched alkane has a spherical or dendritic structure, i.e. has a structure of $R^8R^9CH(CH_2)_n CHR^{10}R^{11}$ or $R^8R^9R_{10}C(CH_2)_nCR^{10}R^{11}R^{12}$, wherein $R^8$-$R^{12}$ has a structure of $R^{13}R^{14}CH(CH_2)_mCHR^{15}R^{16}$ or $R^{13}R^{14}R^{15}C(CH_2)_nCR^{15}R^{16}R^{17}$, $R^{13}$-$R^{17}$ has a structure of $R^{18}R^{19}CH(CH_2)_xCHR^{20}R^{21}$ or $R^{18}R^{19}R^{20}C(CH_2)_x CR^{20}R^{21}R^{22}$, $R^{18}$, $R^{19}$, $R^{20}$, $R^{21}$, $R^{22}$ is hydrogen, straight-chain or branched-chain alkanes, n, m and x is integer of 1 to 500, preferably integer of 1 to 300, more preferably integer of 1 to 100.

The highly branched alkane mixture of the present invention has high viscosity index of about 100-300 (preferably about 150-300), pour point of about −50° C. to about −10° C., and the kinematic viscosity at 100° C. of about 5 to 100 cSt. This kind of alkane mixture is oily polymer, of which the molecular weight is about 500 to 500,000 g/mol and the branching degree (BI) is at least 0.20.

A significant characteristic of the alkane mixture of the present invention is there is about 100 to 500 methyl per 1000 methylene, preferably 200-400, which makes the alkane mixture of the present invention microscopically different from normal linear polymer, show a spherical or dendritic structure, and therefore more suitable for a use as lubricant base oil.

Furthermore, there is about 20-100 ethyl branched-chains, about 2-50 propyl branched-chains, about 20-100 butyl branched-chains, about 2-50 pentyl branched-chains and about 20-200 hexyl or longer branched-chains per 100 methyl branched-chains in the alkane mixture of the present invention.

The bromine number of the alkane mixture of the present invention is low, which meets the requirement of base oil. For example, in one case, the bromine number of an oily polymer polymerized from ethylene catalyzed by a nickel catalyst is 38 g/100 g, and after hydrogenation, the bromine number is reduced to 0.38 g/100 g. In the use of lubricant base oil, the property of such highly-branched oily alkane is superial to current commercial PAO base oil, such as the viscosity index of commercial PAO is about 139, while the viscosity index of highly branched oily alkane obtained in one example of the present invention can reach 261.

In order to improve the physical properties accordingly, various additives or enhancers can be added while this kind of highly-branched saturated alkane is being used, such as antifreeze. In addition, such highly branched saturated hydrocarbon can also be used as an additive to improve resin's processing properties, such as being used as a plasticizer in polymer processing.

The main advantages of the present invention include:

(a) By using a novel catalytic system, firstly high-efficiently realize the preparation of the highly branched oily alkane directly from ethylene, which makes the preparation of base oil no longer dependent on expensive advanced α-olefin and significantly reduce the cost.

(b) Either α-olefin or internal olefin can be directly applied for such purpose and the internal olefin can be better utilized.

(c) Avoiding producing advanced α-olefin as well as PAO from α-olefin.

(d) The highly branched alkanes have low bromine number, high viscosity index, and can be used as base oil for advanced lubricant or processing aids.

With reference to specific embodiment, we further illustrate the present invention. It should be understood that these embodiments are merely intended to illustrate the invention and are no intended to limit the scope of the invention. If we don't indicate specific conditions of experimental methods, follow conventional conditions or in accordance with the conditions recommended by the manufacturer. Unless otherwise indicated, percentage and parts are by weight and percentages by weight.

Example 1

Synthesis of Ligand L1a

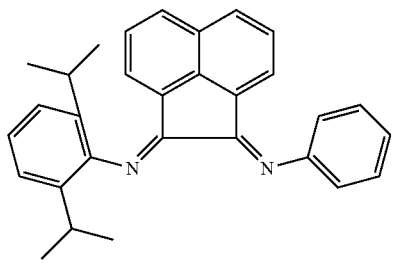 [SMILES: CC(C)c1cccc(C(C)C)c1/N=C1/C(=N/c2ccccc2)c2cccc3cccc1c23]

In 100 mL egg-shaped flask, acenaphthoquinone (3.644 g, 20 mmol), methanol (40 ml), 2,6-diisopropyl aniline (4.0 mL, 20 mmol), two drops of acetic acid were added and the mixture was stirred at room temperature. The reaction was monitored by TLC until ended. The reaction mixture was concentrated under reduced pressure, and purified by column chromatography on alumina N-neutral using EA:PE from 1:20 to 1:10 to give the single imine as orange yellow product (yield 60%). $^1$H NMR (300 MHz, CDCl$_3$): β=8.21 (2H, m), 8.01 (1H, d), 7.82 (1H, t), 7.41 (1H, t), 7.27 (3H, s), 6.64 (1H, d), 2.84 (2H, m), 1.18 (6H, d), 0.90 (6H, d).

In 100 mL egg-shaped flask, the single imine (1.708 g, 5.0 mmol), methanol (40 ml), aniline (7.5 mmol) and two drops of anhydrous acetic acid were added. The reaction mixture was stirred at room temperature. The reaction was monitored by TLC until ended. The reaction mixture was concentrated under reduced pressure, and purified by column chromatography on alumina N-neutral using EA:PE=1:15 to give the orange yellow product L1a. $^1$H NMR (300 MHz, CDCl$_3$): δ=7.88-6.62 (14H, m), 3.06 (2H, m), 1.25-0.93 (12H, d); $^{13}$C NMR (75 MHz, CDCl$_3$): 161.4, 151.6, 147.0, 141.1, 135.4, 130.9, 129.1, 128.7, 128.5, 127.6, 127.4, 124.2, 124.1, 123.6, 123.3, 118.1, 77.0, 28.1, 23.4, 23.3.

Example 2

Synthesis of Ligand L1b

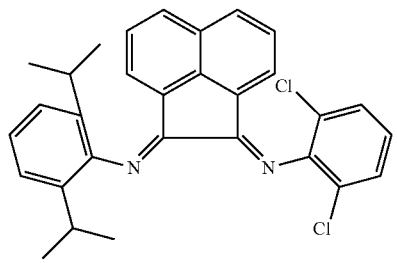 [SMILES: CC(C)c1cccc(C(C)C)c1/N=C1/C(=N/c2c(Cl)cccc2Cl)c2cccc3cccc1c23]

Following the synthesis of ligand L1a of example 1, an orange solid was obtained under the identical operating conditions except that aniline was replaced by 2,6-dichloro aniline in the second step. $^1$H NMR (300 MHz, CDCl$_3$): δ=8.32 (1H, d), 8.10 (1H, d), 7.96 (1.5H, m), 7.53 (2H, d), 7.41 (3H, m), 7.38 (2H, m), 6.91 (0.5H, m), 6.58 (1H, t), 2.77 (2H, m), 1.29 (2H, d), 0.97 (10H, d), $^{13}$C NMR (75 MHz, CDCl3): δ=162.2, 157.8, 146.1, 133.1, 130.7, 127.5, 124.8, 124.4, 124.3, 123.39, 123.1, 122.7, 120.7, 77.4, 77.6, 28.5, 27.9, 23.5, 22.8. IR (KBr): ν(cm$^{-1}$)=3052, 2960, 2923, 2865, 1674, 1640, 1602, 1463, 1433, 1242, 1077, 1033, 831, 779, 760, 730; C$_{30}$H$_{26}$Cl$_2$N$_2$ (484.45): Anal. Calc. C, 74.22; H, 5.40; N, 5.77. Found C, 73.99; H, 5.39; N, 5.65.

Example 3

Synthesis of Ligand L1c

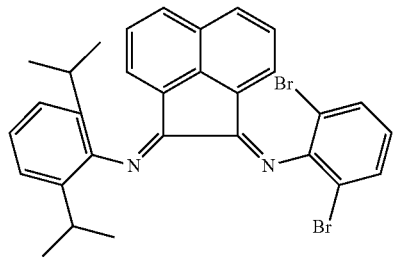 [SMILES: CC(C)c1cccc(C(C)C)c1/N=C1/C(=N/c2c(Br)cccc2Br)c2cccc3cccc1c23]

Following the synthesis of ligand L1a in example 1, an orange red solid was obtained under the identical operating conditions except that aniline was replaced by 2,6-dibromoaniline in the second step. $^1$H NMR (300 MHz, CDCl$_3$): δ=8.33 (1H, d), 8.05 (1H, d), 7.91 (2H, m), 7.69 (1.5H, d), 7.49 (2H, d), 7.28 (1H, m), 7.15 (2H, s), 6.71 (1H, m), 6.69 (1H, t), 6.51 (0.5H, d), 1.23 (2H, d), 0.97 (10H, d); $^{13}$C NMR (75 MHz, CDCl3): δ=162.2, 157.5, 149.1, 146.2, 141.2, 135.3, 134.7, 131.3, 128.9, 124.4, 120.8, 112.1, 77.0, 58.4, 28.0, 23.8, 23.1, 23.0, 18.4. IR (KBr): ν(cm$^{-1}$)=3058, 2960, 2922, 2865, 1677, 1640, 1594, 1547, 1462, 1425, 1282, 1241, 1080, 1032, 925, 831, 792, 778, 759, 725; C$_{30}$H$_{26}$Br$_2$N$_2$ (574.35): Anal. Calc. C, 62.74; H, 4.56; N, 4.88. Found C, 62.69; H, 4.60; N, 4.73.

Example 4

Synthesis of Ligand L1d

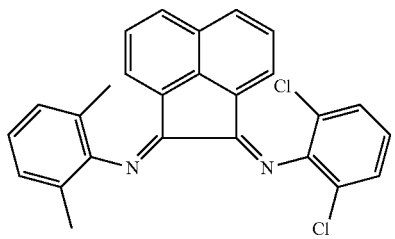 [SMILES: Cc1cccc(C)c1/N=C1/C(=N/c2c(Cl)cccc2Cl)c2cccc3cccc1c23]

In 100 mL egg-shaped flask, acenaphthoquinone (1.822 g, 10 mmol), 2,6-dichloroaniline (1.620 g, 10 mmol), TsOH (190 mg, 1 mmol) and toluene (50 mL) were added. The reaction mixture was stirred at reflux with water separating for 3 h. The reaction was monitored by TLC until ended. The reaction mixture was cooled, then concentrated under reduced pressure, and purified by column chromatography on alumina N-neutral using EA:PE=1:20 to give the single imine as an orange product. $^1$H NMR (300 MHz, CDCl$_3$): δ=8.28-6.92 (9H, m); IR (KBr): ν(cm$^{-1}$)=3059, 1734, 1651, 1600, 1590, 1558, 1279, 1233, 1151, 1072, 1028, 910, 832, 791, 778, 768, 745, 687.

In 100 mL egg-shaped flask, the single imine (1.631 g, 5.0 mmol), methanol (30 ml), two drops of anhydrous acetic acid and 2,6-dimethylanile (0.93 mL, 7.5 mmol) were added. The reaction mixture was stirred at room temperature. The reaction was monitored by TLC until ended. The reaction mixture was concentrated under reduced pressure, and was purified by column chromatography on alumina N-neutral using EA:PE=1:15 to give the orange yellow product. $^1$H NMR (300 MHz, CDCl$_3$): δ=8.30-6.57 (12H, m), 2.15-1.90 (6H, s); $^{13}$C NMR (75 MHz, CDCl3): δ=162.7, 157.4, 148.8, 141.5, 131.0, 130.7, 129.3, 128.9, 128.5, 128.3, 128.1, 127.6, 124.9, 124.7, 124.5, 123.9, 123.0, 122.7, 122.3, 120.7, 77.0, 17.8, 17.6; IR (KBr): ν(cm$^{-1}$)=3059, 2918, 1681, 1640, 1592, 1557, 1469, 1431, 1282, 1243, 1199, 1075, 1031, 924, 828, 774, 764, 729; Anal. Calcd. C, 72.73; H, 4.23; N, 6.52. Found C, 73.01; H, 4.21; N, 6.46.

Example 5

Synthesis of Ligand L1e

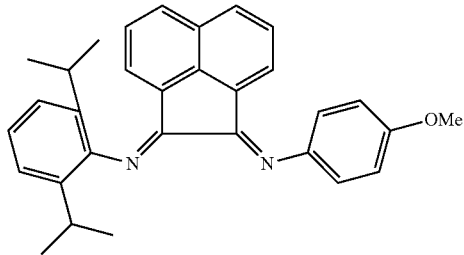 [SMILES: COc1ccc(/N=C2/C(=N/c3c(C(C)C)cccc3C(C)C)c3cccc4cccc2c34)cc1]

Following the synthesis of ligand L1a in example 1, an orange red solid was obtained with the identical operating conditions except that aniline was replaced by p-methoxyaniline in the second step. $^1$H NMR (300 MHz, CDCl$_3$): δ=7.94-6.61 (13H, m), 3.00-2.52 (2H, m), 1.26-0.91 (12H, d); $^{13}$C NMR (75 MHz, CDCl$_3$): 161.3, 154.7, 146.9, 141.4, 135.5, 131.2, 129.4, 129.1, 129.0, 128.3, 128.0, 127.6, 126.7, 124.5, 123.8, 123.7, 123.6, 123.2, 118.5, 117.7, 77.0, 28.3, 23.5, 23.4, 23.1, 22.3; Anal. Calcd. C, 76.84; H, 5.62; N, 5.78. Found C, 76.63; H, 5.62; N, 5.73.

Example 6

Synthesis of Ligand L1f

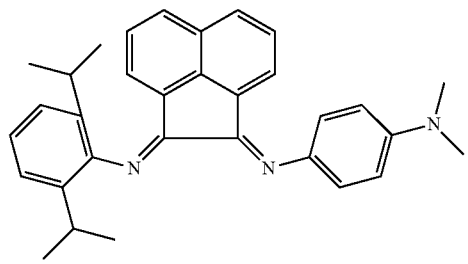 [SMILES: CC(C)c1cccc(C(C)C)c1/N=C1/C(=N/c2ccc(N(C)C)cc2)c2cccc3cccc1c23]

Following the synthesis of ligand L1a in example 1, an orange red solid was obtained with the identical operating conditions except that aniline was replaced by N,N-dimethyl aniline in the second step. $^1$H NMR (300 MHz, CDCl$_3$): δ=8.18-6.58 (13H, m), 3.04 (8H, m), 1.22-0.91 (12H, d); $^{13}$C NMR (75 MHz, CDCl$_3$): 161.8, 159.2, 148.3, 147.4, 141.0, 135.6, 129.5, 129.2, 128.7, 128.3, 127.5, 124.1, 123.4, 123.3, 123.0, 120.7, 112.9, 77.0, 40.8, 28.3, 28.2, 23.7, 23.4, 23.3.

Example 7

Synthesis of Ligand L1g

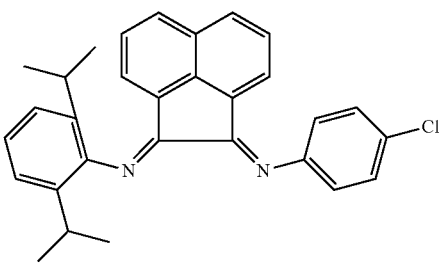 [SMILES: CC(C)c1cccc(C(C)C)c1/N=C1/C(=N/c2ccc(Cl)cc2)c2cccc3cccc1c23]

Following the synthesis of ligand L1a in example 1, an orange red solid was obtained with the identical operating conditions except that aniline was replaced by p-chloroaniline in the second step. $^1$H NMR (300 MHz, CDCl$_3$): δ=8.17-6.60 (13H, m), 3.01-2.97 (2H, m), 1.23-0.93 (12H, d); $^{13}$C NMR (75 MHz, CDCl$_3$): 161.4, 160.9, 150.1, 147.0, 131.1, 141.2, 129.5, 129.4, 129.1, 128.9, 128.4, 128.2, 127.8, 127.5, 124.4, 124.1, 123.7, 123.5, 123.1, 119.8, 119.2, 77.4, 77.0, 28.2, 23.5, 23.4, 23.3, 23.1; Anal. Calcd. C, 79.89; H, 6.03; N, 6.21. Found C, 79.82; H, 6.13; N, 6.07.

Example 8

Synthesis of Ligand L1h

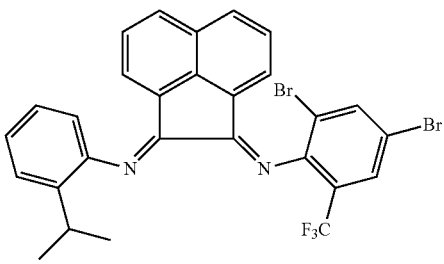 [SMILES: CC(C)c1ccccc1/N=C1/C(=N/c2c(Br)cc(Br)cc2C(F)(F)F)c2cccc3cccc1c23]

In 100 mL egg-shaped flask, acenaphthoquinone (1.093 g, 6.0 mmol), methanol (40 ml), 4,6-dibromo-2-(trifluoromethyl)aniline (2.105 g, 6.6 mmol) and two drops of anhydrous acetic acid were added. The reaction mixture was stirred at reflux. The reaction was monitored by TLC until ended. The reaction mixture was concentrated under reduced pressure, and methanol (20 mL) was added to the crude product, which was filtered after frozen in the freezer, to obtain the single imine as a red product. $^1$H NMR (300 MHz, CDCl$_3$): δ=6.846-8.245 (8H, m). $^{13}$C NMR (75 MHz, CDCl$_3$): δ=187.9, 184.5, 162.8, 161.0, 147.3, 144.4, 139.0, 138.2, 132.3, 130.6, 130.2, 129.5, 129.1, 128.9, 128.6, 128.4, 128.3, 123.1, 122.6, 122.4, 121.3, 117.2, 115.5, 113.3, 77.0; Anal. Calc. C, 47.24; H, 1.67; N, 2.90. Found C, 47.04; H, 1.90; N, 2.88. MS(ESI)(m/z): 483.7 (M+1).

In 100 mL egg-shaped flask, the single imine (1.449 g, 3 mmol), methanol (40 ml), 2-isopropylaniline (0.39 mL, 3.15 mmol) and two drops of anhydrous acetic acid were added. The reaction mixture was stirred at reflux. The reaction was monitored by TLC until ended. The reaction mixture was concentrated under reduced pressure, and purified by column chromatography on alumina N-neutral using CH$_2$Cl$_2$:PE=1:2 to give the orange yellow product, which was then crystallized from methanol to give the diimine. $^1$H NMR (300 MHz, CDCl$_3$): δ=8.27-6.70 (12H, m), 3.16-2.64 (1H, m), 1.25-0.96 (6H, m); $^{13}$C NMR (75 MHz, CDCl$_3$): δ=163.0, 147.7, 137.8, 132.7, 130.8, 128.9, 128.6, 128.4, 127.8, 126.3, 125.9, 125.4, 123.6, 121.0, 116.6, 114.1, 113.9, 77.0, 28.4, 23.0, 22.7; Anal. Calc. C, 56.02; H, 3.19; N, 4.67. Found C, 56.05; H, 3.20; N, 4.52.

Example 9

Synthesis of Ligand L1i

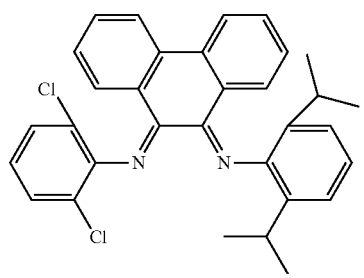 [SMILES: CC(C)c1cccc(C(C)C)c1/N=C1/C(=N/c2c(Cl)cccc2Cl)c2ccccc2-c2ccccc21]

In 250 mL egg-shaped flask, phenanthrene-9,10-dione (2.0 g, 9.6 mmol), 2,6-diisopropylaniline (3.2 mL, 16.9 mmol), ten drops of anhydrous formic acid and 120 ml methanol were added. The reaction mixture was heated at reflux for 24 h. The reaction was monitored by TLC until ended. The reaction mixture was cooled in the freezer at −20° C. overnight, and was filtered to give the single imine as a green product. $^1$H NMR (300 MHz, CDCl$_3$): δ=8.38 (1H, d), 8.06-7.98 (3H, d), 7.70-7.63 (2H, m), 7.50 (1H, t), 7.38 (1H, t), 7.18 (2H, d), 7.10 (1H, m), 2.66 (2H, m), 1.28-1.04 (12H, d).

In 50 mL egg-shaped flask, the single imine (311.4 mg, 1 mmol), methanol (25 ml), 2,6-dichloroaniline (199.4 mg, 1.2 mmol) were added. The reaction mixture was stirred at reflux. The reaction was monitored by TLC until ended. The reaction mixture was concentrated under reduced pressure, and purified by column chromatography on alumina N-neutral using EA:PE=1:50 to give the scarlet product, which was crystallized from methanol to give the L1i. $^1$H NMR (300 MHz, CDCl$_3$): δ=8.46 (1H, d), 8.46-6.83 (14H, m), 2.77-1.96 (2H, m), 0.82-0.67 (12H, d); $^{13}$C NMR (75 MHz, CDCl$_3$): δ=162.2, 158.3, 146.4, 145.3, 135.0, 134.6, 134.4, 132.7, 132.3, 129.1, 129.0, 128.0, 127.8, 127.6, 127.1, 124.4, 124.2, 124.0, 123.5, 123.4, 123.2, 77.0, 27.6, 23.8, 22.7; Anal. Calcd. C, 75.14; H, 5.52; N, 5.48. Found C, 74.94; H, 5.49; N, 5.32.

Example 10

Synthesis of Ligand L1j

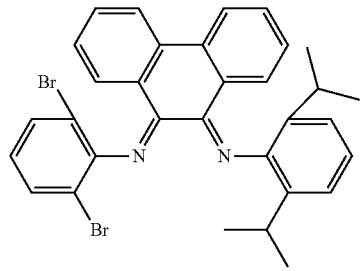 [SMILES: CC(C)c1cccc(C(C)C)c1/N=C1/C(=N/c2c(Br)cccc2Br)c2ccccc2-c2ccccc21]

Following the procedure in example 9, the ligand L1j was obtained except that 2,6-dichloroaniline was replaced by 2,6-dibromoaniline in the second step. $^1$H NMR (300 MHz, CDCl$_3$): δ=8.48-6.77 (14H, m), 2.79-1.97 (2H, m), 1.13-0.69 (12H, m); $^{13}$C NMR (75 MHz, CDCl$_3$): δ=161.4, 158.0, 149.0, 145.3, 135.0, 134.6, 134.4, 132.7, 132.2, 131.3, 131.2, 129.2, 129.0, 128.0, 127.8, 127.1, 124.4, 124.2, 124.1, 123.5, 123.4, 113.3, 77.0, 27.6, 23.9, 22.9.

Example 11

Synthesis of Ligand L1k

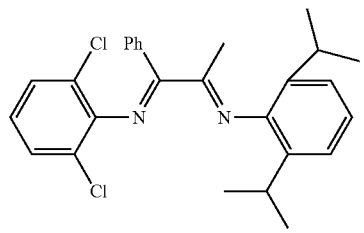 [SMILES: CC(=N\c1c(C(C)C)cccc1C(C)C)/C(=N/c1c(Cl)cccc1Cl)c1ccccc1]

In 50 mL egg-shaped flask, 1-phenylpropane-1,2-dione (1.4 mL, 10.5 mmol), 2,6-diisopropylaniline (2.2 mL, 10.5 mmol), six drops of formic acid and methanol (3 ml) were added. The reaction mixture was stirred at room temperature for 12 h. The reaction was monitored by TLC until ended. The reaction mixture was concentrated under reduced pressure, and purified by column chromatography on alumina N-neutral using EA:PE=1:50 to give the product, which was crystallized from methanol, and then filtered to give the single imine as a yellow solid. $^1$H NMR (300 MHz, CDCl$_3$): δ=8.22 (2H, d), 7.60 (1H, t), 7.52 (2H, t), 7.19 (3H, m), 2.79 (2H, m), 2.04 (3H, s), 1.22 (2H, d), 1.17 (2H, d).

In 50 mL egg-shaped flask, the single imine (307.4 mg, 1 mmol), methanol (25 ml), 2,6-dichloroaniline (178.2 mg, 1.1 mmol) and two drops of acetic acid were added. The reaction mixture was stirred at reflux. The reaction was monitored by TLC until ended. The reaction mixture was concentrated under reduced pressure, and purified by column chromatography on alumina N-neutral using EA:PE=1:50 to give the yellow product, which was crystallized from methanol to give the L1k. $^1$H NMR (300 MHz, CDCl$_3$): δ=8.10-6.74 (11H, m), 2.68-2.33 (2H, m), 2.24-1.83 (3H, s), 1.21-1.05 (12H, d); $^{13}$C NMR (75 MHz, CDCl$_3$): δ=171.5, 168.1, 146.1, 145.4, 135.2, 134.6, 135.2, 134.6, 128.9, 128.7, 128.5, 127.8, 127.2, 124.3, 123.9, 123.7, 123.2, 122.8, 77.0, 28.4, 27.6, 23.9, 23.7, 22.9, 22.6, 17.6; Anal. Calc. C, 71.84; H, 6.25; N, 6.21. Found C, 72.10; H, 6.52; N, 5.92.

Example 12

Synthesis of Ligand L1l

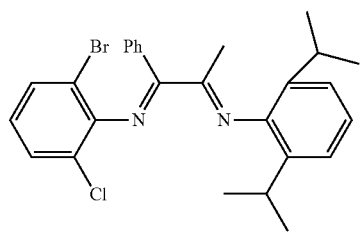 [SMILES: CC(=N\c1c(C(C)C)cccc1C(C)C)/C(=N/c1c(Cl)cccc1Br)c1ccccc1]

Following the synthesis of ligand L1k in example 11, an orange red solid was obtained with the identical operating conditions except that 2,6-dichloroaniline was replaced by 2,6-dibromoaniline in the second step. $^1$H NMR (300 MHz, CDCl$_3$): δ=8.01-6.67 (11H, m), 2.71-2.30 (2H, m), 2.26-1.86 (3H, s), 1.22-1.07 (12H, d); $^{13}$C NMR (75 MHz, CDCl$_3$): δ=170.7, 168.4, 147.8, 146.2, 134.7, 131.7, 131.6, 129.1, 128.7, 127.7, 127.2, 125.2, 123.8, 122.8, 119.3, 113.1, 77.0, 28.4, 23.0, 22.7, 27.7, 17.8; MS(ESI)(m/z): 541 (M+1).

Example 13

Synthesis of Ligand L1m

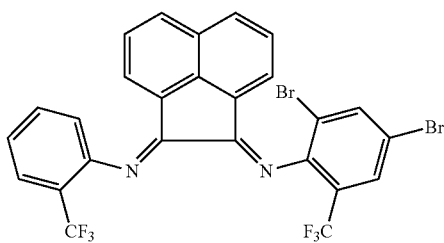 [SMILES: FC(F)(F)c1ccccc1/N=C1/C(=N/c2c(Br)cc(Br)cc2C(F)(F)F)c2cccc3cccc1c23]

Following the procedure in example 8, the ligand L1m was obtained except that o-isopropylaniline was replaced by o-trifluoromethylaniline in the second step. $^1$H NMR (300 MHz, CDCl$_3$): δ=8.27-6.62 (12H, m).

Example 14

Synthesis of Ligand L1n

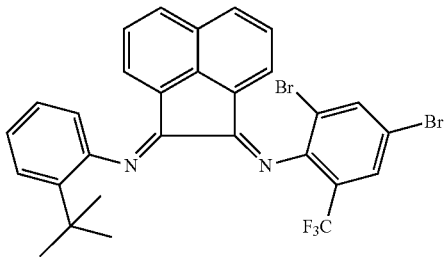 [SMILES: CC(C)(C)c1ccccc1/N=C1/C(=N/c2c(Br)cc(Br)cc2C(F)(F)F)c2cccc3cccc1c23]

Following the procedure in example 8, the ligand L1n was obtained except that o-isopropylaniline was replaced by o-tert-butyl-aniline in the second step. $^1$H NMR (300 MHz, CDCl$_3$): δ=8.26-6.50 (12H, m), 1.33-1.02 (9H, m); Anal. Calc. C, 56.70; H, 3.45; N, 4.56. Found C, 56.56; H, 3.33; N, 4.32.

Example 15

Synthesis of Ligand L1o

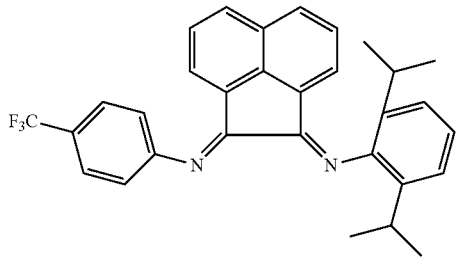 [SMILES: CC(C)c1cccc(C(C)C)c1/N=C1/C(=N/c2ccc(C(F)(F)F)cc2)c2cccc3cccc1c23]

Following the procedure in example 1, the ligand L1o was obtained except that aniline was replaced by p-trifluoromethyl aniline in the second step. $^1$H NMR (300 MHz, CDCl$_3$): δ=7.94-6.61 (13H, m), 3.00-2.52 (2H, m), 1.26-0.91 (12H, d); $^{13}$C NMR (75 MHz, CDCl$_3$): 161.3, 154.7, 146.9, 141.4, 135.5, 131.2, 129.4, 129.1, 129.0, 128.3, 128.0, 127.6, 126.7, 124.5, 123.8, 123.7, 123.6, 123.2, 118.5, 117.7, 77.0, 28.3, 23.5, 23.4, 23.1, 22.3; Anal. Calcd. C, 76.84; H, 5.62; N, 5.78. Found C, 76.63; H, 5.62; N, 5.73.

Example 16

Synthesis of Ligand L1p

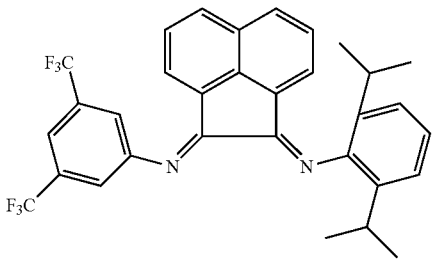 [SMILES: CC(C)c1cccc(C(C)C)c1/N=C1/C(=N/c2cc(C(F)(F)F)cc(C(F)(F)F)c2)c2cccc3cccc1c23]

Following the procedure in example 1, the ligand L1p was obtained except that aniline was replaced by 3,5-bis(trifluoromethyl) aniline in the second step. $^1$H NMR (300 MHz, CDCl$_3$): δ=8.08-6.47 (12H, m), 2.98-2.48 (2H, m), 1.24-0.88 (12H, m); $^{13}$C NMR (75 MHz, CDCl$_3$): 162.3, 161.1, 153.2, 152.8, 146.7, 146.3, 141.5, 140.8, 135.4, 134.3, 133.4, 133.0, 132.7, 131.9, 131.6, 130.8, 130.0, 129.5, 129.1, 128.9, 128.5, 128.1, 128.0, 127.7, 124.7, 124.6, 124.5, 123.9, 123.6, 123.5, 123.3, 123.2, 120.4, 119.2, 117.8, 116.3, 77.0, 28.4, 23.6, 23.5, 22.8, 22.6.

Example 17

Synthesis of Ligand L1q

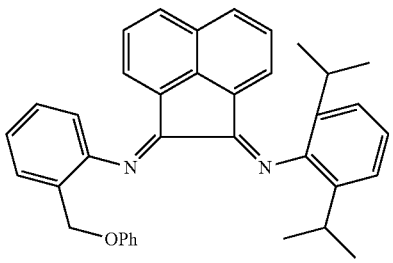 [SMILES: CC(C)c1cccc(C(C)C)c1/N=C1/C(=N/c2ccccc2COc2ccccc2)c2cccc3cccc1c23]

Following the procedure in example 1, the ligand L1q was obtained except that aniline was replaced by o-phenoxymethylene aniline in the second step. $^1$H NMR (300 MHz, CDCl$_3$): δ=7.93-6.44 (18H, m), 5.03 (2H, s), 2.82 (2H, m), 1.14-0.84 (12H, d); $^{13}$C NMR (75 MHz, CDCl$_3$): 161.5, 161.2, 158.3, 150.5, 146.9, 141.1, 135.4, 130.9, 129.5, 129.1, 128.9, 127.7, 125.2, 124.3, 124.0, 123.4, 123.3, 120.4, 117.6, 113.9, 77.0, 66.6, 50.7, 28.3, 23.2, 23.1.

Example 18

Synthesis of Complex 1a

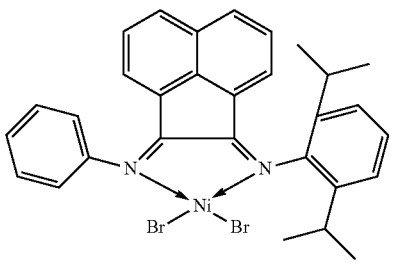

In a glovebox, to a 50 ml Schlenk tube was add NiBr$_2$ (DME) (1 mmol), and then L1a (1.05 mmol). After being purged with nitrogen for three times, dichloromethane (20 mL) was added. The reaction was stirred overnight. The reaction mixture was transferred into another 50 ml Schlenk tube by a double-ended needle and concentrated. Then the residue was washed by a mixture of dichloromethane (2 mL) and n-hexane (20 mL) for 2-3 times and filtered. The solid was dried in vacuo. Wash the Schlenk tube in the glovebox with hexane and then filtered, and the solid was collected as a red product Anal. Calcd. For C$_{30}$H$_{28}$Br$_2$N$_2$Ni: C, 56.74; H, 4.44; N, 4.41. Found: C, 56.14; H, 4.65; N, 4.25.

Example 19

Synthesis of Complex 1b

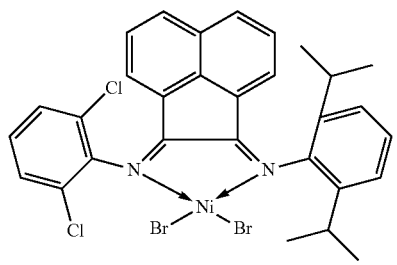

A reddish brown complex was obtained by the same procedure as example 18 except that ligand L1a was replaced by ligand L1b, yield 85%. Anal. Calcd. For C$_{30}$H$_{26}$Br$_2$Cl$_2$N$_2$Ni: C, 51.19; H, 3.72; N, 3.98. Found: C, 51.25; H, 3.64; N, 3.64.

Example 20

Synthesis of Complex 1c

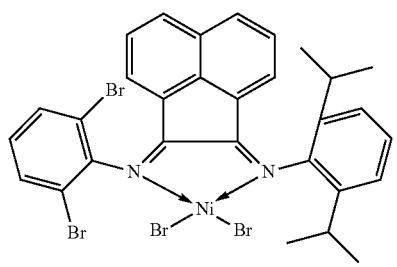

A reddish brown complex was obtained by the same procedure as example 18 except that ligand La was replaced by ligand L1c, yield 90%. Anal. Calcd. For C$_{30}$H$_{26}$Br$_4$N$_2$Ni: C, 45.45; H, 3.31; N, 3.53. Found: C, 45.82; H, 3.30; N, 3.30.

Example 21

Synthesis of Complex 1d

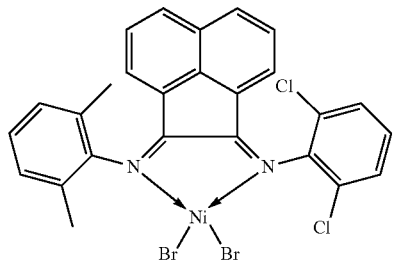

A reddish brown complex was obtained by the same procedure as example 18 except that ligand La was replaced by ligand L1d, yield 72%. Anal. Calcd. For $C_{26}H_{18}Br_2Cl_2N_2Ni$: C, 48.20; H, 2.80; N, 4.32. Found: C, 47.58; H, 2.99; N, 4.02.

Example 22

Synthesis of Complex 1e

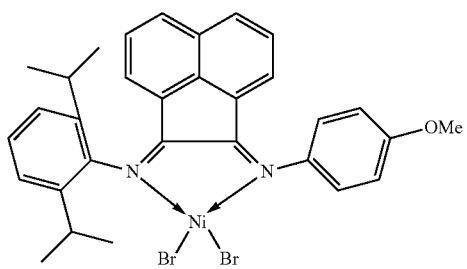

A reddish brown complex was obtained by the same procedure as example 18 except that ligand L1a was replaced by ligand L1e, yield 30%. Anal. Calcd. C, 55.98; H, 4.55; N, 4.21. Found: C, 56.24; H, 4.71; N, 3.94.

Example 23

Synthesis of Complex 1f

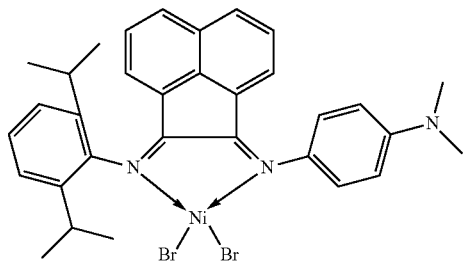

A reddish brown complex was obtained by the same procedure as example 18 except that ligand L1a was replaced by ligand L1f, yield 60%. Anal. Calcd. C, 56.68; H, 4.90; N, 6.20. Found: C, 56.93; H, 5.13; N, 5.91.

Example 24

Synthesis of Complex 1g

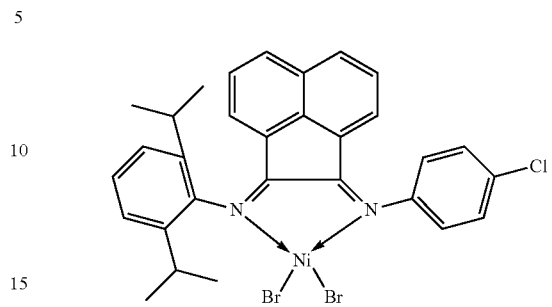

A reddish brown complex was obtained by the same procedure as example 18 except that ligand L1a was replaced by ligand L1g, yield 31%. Anal. Calcd. C, 53.82; H, 4.06; N, 4.18. Found: C, 54.41; H, 4.07; N, 3.92.

Example 25

Synthesis of Complex 1h

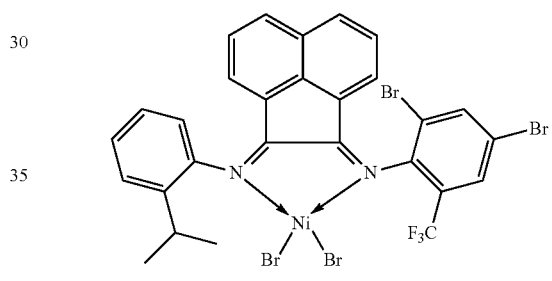

A reddish brown complex was obtained by the same procedure as example 18 except that ligand L1a was replaced by ligand L1h, yield 75%. Anal. Calcd. C, 41.07; H, 2.34; N, 3.42. Found: C, 41.34; H, 2.54; N, 3.92.

Example 26

Synthesis of Complex 1i

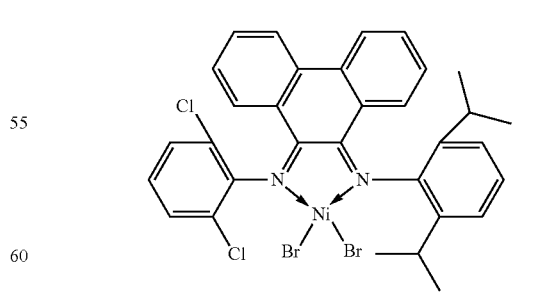

A reddish brown complex was obtained by the same procedure as example 18 except that ligand L1a was replaced by ligand L1i, yield 20%. Anal. Calcd. C, 52.65; H, 3.87; N, 3.84. Found: C, 52.90; H, 3.98; N, 3.92.

Example 27

Synthesis of Complex 1j

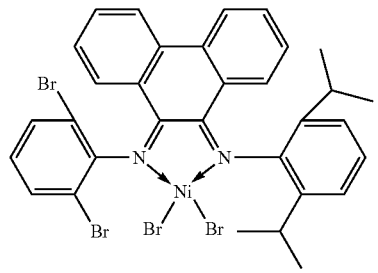

A reddish brown complex was obtained by the same procedure as example 18 except that ligand L1a was replaced by ligand L1j, yield 30%. Anal. Calcd. C, 46.93; H, 3.45; N, 3.42. Found: C, 46.50; H, 3.23; N, 3.32.

Example 28

Synthesis of Complex 1k

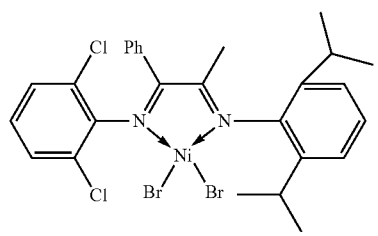

A reddish brown complex was obtained by the same procedure as example 18 except that ligand L1a was replaced by ligand L1k, yield 15%. Anal. Calcd. C, 48.41; H, 4.21; N, 4.18. Found: C, 48.20; H, 4.00; N, 4.02.

Example 29

Synthesis of Complex 1l

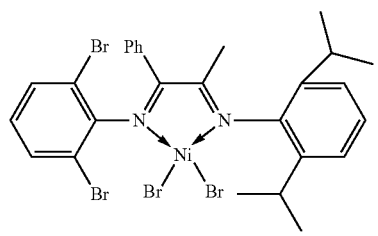

A reddish brown complex was obtained by the same procedure as example 18 except that ligand L1a was replaced by ligand L1l, yield 10%. Anal. Calcd. C, 42.74; H, 3.72; N, 3.69. Found: C, 42.50; H, 3.56; N, 3.52.

Example 30

Synthesis of complex 1m

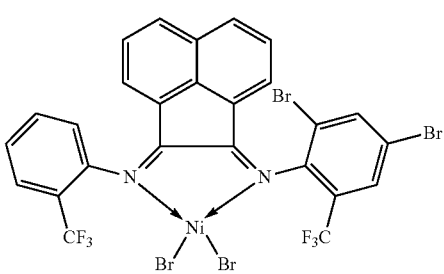

A reddish brown complex was obtained by the same procedure as example 18 except that ligand L1a was replaced by ligand L1m, yield 60%. Anal. Calcd. C, 36.97; H, 1.43; N, 3.32. Found: C, 36.87; H, 1.32; N, 3.22.

Example 31

Synthesis of Complex 1n

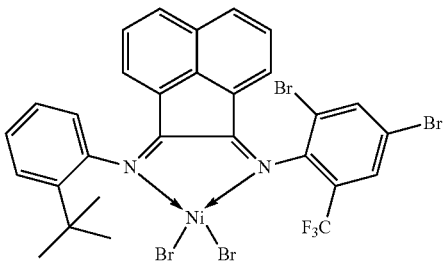

A reddish brown complex was obtained by the same procedure as example 18 except that ligand L1a was replaced by ligand L1n, yield 50%. Anal. Calcd. C, 41.82; H, 2.54; N, 3.36. Found: C, 41.90; H, 2.40; N, 3.42.

Example 32

Synthesis of Complex 1o

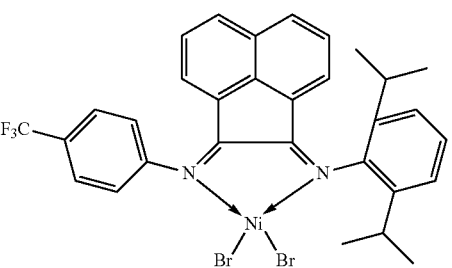

A reddish brown complex was obtained by the same procedure as example 18 except that ligand L1a was replaced by ligand L1o, yield 35%. Anal. Calcd: C, 52.96; H, 3.87; N, 3.98. Found: C, 53.15; H, 3.93; N, 4.12.

Example 33

Synthesis of Complex 1p

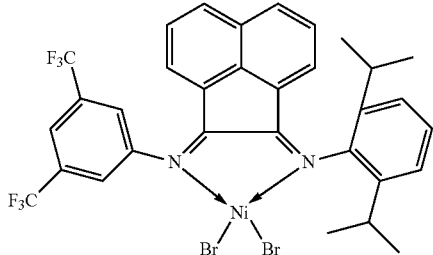

A reddish brown complex was obtained by the same procedure as example 18 except that ligand L1a was replaced by ligand L1p, yield 70%. Anal. Calcd: C, 49.85; H, 3.40; N, 3.63. Found: C, 49.80; H, 3.38; N, 3.57.

Example 34

Synthesis of Complex 1q

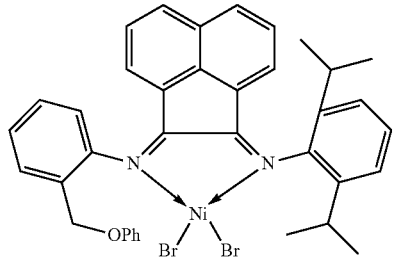

A reddish brown complex was obtained by the same procedure as example 18 except that ligand L1a was replaced by ligand L1q, yield 70%. Anal. Calcd: C, 59.96; H, 4.62; N, 3.78. Found: C, 60.80; H, 4.96; N, 3.62.

Example 35

Synthesis of Complex 1r

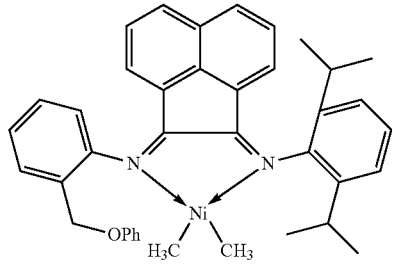

React complex 1q with methylmagnesium bromide, to obtain complex 1r. Anal. Calcd: C, 76.61; H, 6.59; N, 4.58. Found: C, 77.01; H, 6.89; N, 4.89.

Example 36

Synthesis of Complex 1t

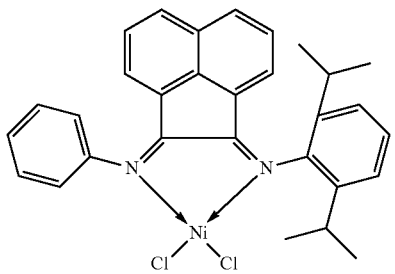

Complex 1t was obtained by the same procedure as example 18 except that (DME)NiBr$_2$ was replaced by (DME)NiCl$_2$.

Anal. Calcd. C, 65.97; H, 5.17; N, 5.13. Found: C, 65.81; H, 5.00; N, 5.02.

Example 37

Synthesis of Complex 1u

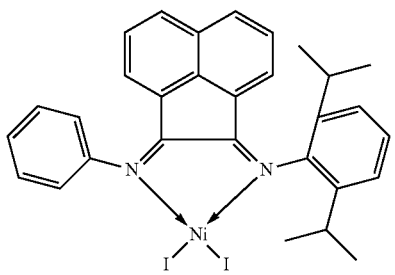

Complex 1u was obtained by the same procedure as example 18 except that (DME)NiBr$_2$ was replaced by (DME)NiI$_2$.

Anal. Calcd. C, 49.42; H, 3.87; N, 3.84. Found: C, 49.85; H, 4.12; N, 4.00.

Example 38

Synthesis of Complex 1v

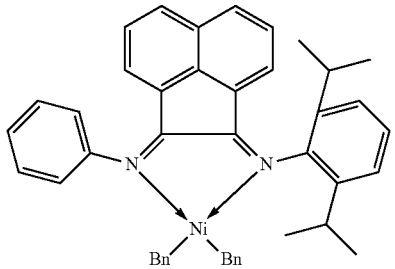

React complex 1a with benzylmagnesium bromide to obtain complex 1v. Anal. Calcd. C, 80.37; H, 6.44; N, 4.26. Found: C, 80.90; H, 6.85; N, 4.40.

Example 39

A Schlenk flask (200 mL) was purged firstly with nitrogen, then vacuumized and then purged with ethylene. Under the atmosphere of ethylene, 25 mL DCE and then AlEt$_2$Cl (0.9M in toluene, 0.30 mL) were added. Then complex 1a (5 µmol) was added at 60° C. and under 1 atm and the reaction mixture was stirred for 30 min. When the reaction completed, stop purging ethylene and concentrate the reaction mixture. The residue was purified by silica gel column with petroleum ether. The filtrate was concentrated to obtain oily polyethylene. Activity: 3.0×10$^6$ g/mol·h·atm. $^1$HNMR 250 Me/1000 CH$_2$. Bromine number: 38 g/100 g. Molecular Weight (Mn): 2000 g/mol.

Example 40

Repeat the procedure of example 39, the difference is that using complex 1b (2 umol) instead of complex 1a, and co-catalyst AlEt$_2$Cl (0.22 mL, 0.9M in toluene) was added.
Result: 7.0 g oily polyethylene was obtained. Activity: 7.0×10$^6$ g/mol·h·atm. Bromine number: 33 g/100 g. Mn: 50,000 g/mol.

Example 41

Repeat the procedure of example 39, the difference is that using complex 1c (2 µmol) instead of complex 1a.
Result: 9.0 g oily polyethylene. Activity: 9.0×10$^6$ g/mol·h·atm, bromine number 35 g/100 g. $M_{w, GPC}$ 4,570 g/mol, $M_{w, LLS}$ 46,400 g/mol. It should be noted that the ratio of Mw, LLS and Mw, GPC reached 10:1, which indicated that the structure of the highly branched polyethylene is spherical.

Example 42

Repeat the procedure of example 39, the difference is that using complex 1d (5 µmol) instead of complex 1a.
Result: 2.5 g oily polyethylene was obtained. Activity: 1.0×10$^6$ g/mol·h·atm. $^1$HNMR 260 Me/1000 CH$_2$.

Example 43

Repeat the procedure of example 39, the difference is that using complex 1e (5 µmol) instead of complex 1a.
Result: 5.0 g oily polyethylene was obtained. Activity: 2.0×10$^6$ g/mol·h·atm, $^1$HNMR 280 Me/1000 CH$_2$.

Example 44

Repeat the procedure of example 39, the difference is that using complex 1f (5 µmol) instead of complex 1a.
Result: 5.0 g oily polyethylene was obtained. Activity: 2.0×10$^6$ g/mol·h·atm. $^1$HNMR 270 Me/1000 CH$_2$. Bromine number 40 g/100 g.

Example 45

Repeat the procedure of example 39, the difference is that using complex 1g (5 µmol) instead of complex 1a.
Result: 5.0 g oily polyethylene was obtained. Activity: 2.0×10$^6$ g/mol·h·atm, $^1$HNMR 200 Me/1000 CH$_2$.

Example 46

Repeat the procedure of example 39, the difference is that using complex 1h (5 µmol) instead of complex 1a.
Result: 2.5 g oily polyethylene was obtained. Activity: 1.0×10$^6$ g/mol·h·atm, $^1$HNMR 280 Me/1000 CH$_2$. Bromine number: 60 g/100 g.

Example 47

Repeat the procedure of example 39, the difference is that using complex 1i (1 µmol) instead of complex 1a and the time of polymerization is 5 min.
Result: 4.2 g oily polyethylene was obtained. Activity: 5.0×10$^7$ g/mol·h·atm, $^1$HNMR 200 Me/1000 CH$_2$. Mn: 110,000 g/mol.

Example 48

Repeat the procedure of example 39, the difference is that using complex 1j (1 µmol) instead of complex 1a.
Result: 10.0 g oily polyethylene was obtained. Activity: 4.0×10$^6$ g/mol·h·atm, $^1$HNMR 200 Me/1000 CH$_2$. Bromine number: 30 g/100 g. Mn: 120,000 g/mol.

Example 49

Repeat the procedure of example 39, the difference is that using complex 1k (1 µmol) instead of complex 1a.
Result: oily polyethylene was obtained. Activity: 5.0×10$^6$ g/mol·h·atm. $^1$HNMR 110 Me/1000 CH$_2$. Bromine number: 25 g/100 g.

Example 50

Repeat the procedure of example 39, the difference is that using complex 1l (5 µmol) instead of complex 1a.
Result: oily polyethylene was obtained. Activity: 6.0×10$^6$ g/mol·h·atm, $^1$HNMR 130 Me/1000 CH$_2$.

Example 51

Repeat the procedure of example 39, the difference is that using complex 1m (5 µmol) instead of complex 1a.
Result: oily polyethylene was obtained. Activity: 4.5×10$^6$ g/mol·h·atm, $^1$HNMR 190 Me/1000 CH$_2$. Bromine number 40 g/100 g.

Example 52

Repeat the procedure of example 39, the difference is that using complex 1n (1 µmol) instead of complex 1a.
Result: oily polyethylene was obtained. Activity: 8×10$^6$ g/mol·h·atm, $^1$HNMR 165 Me/1000 CH$_2$.

Example 53

Repeat the procedure of example 39, using complex 1o (5 µmol) instead of complex 1a.
Result: oily polyethylene was obtained. Activity: 2.0×10$^6$ g/mol·h·atm, $^1$HNMR 280 Me/1000 CH$_2$. Bromine number 55 g/100 g.

Example 54

Repeat the procedure of example 39, the difference is that using complex 1p (5 µmol) instead of complex 1a.
Result: oily polyethylene was obtained. Activity: 2.0×10$^6$ g/mol·h·atm, $^1$HNMR 320 Me/1000 CH$_2$.

Example 55

Repeat the procedure of example 39, the difference is that using complex 1q (5 µmol) instead of complex 1a.

Result: oily polyethylene was obtained. Activity: $1.0 \times 10^6$ g/mol·h·atm, $^1$HNMR 300 Me/1000 $CH_2$.

Example 56 (Alkyl Nickel Catalyst)

Repeat the procedure of example 39, the difference is that using complex 1r (5 µmol) instead of complex 1a, and adding co-catalyst MMAO (0.30 mL, 1.9 M).
Result: oily polyethylene was obtained. Activity: $8.0 \times 10^6$ g/mol·h·atm, $^1$HNMR 150 Me/1000 $CH_2$.

Example 57 (Solvent Toluene)

Repeat the procedure of example 39, the difference is that using complex 1j (5 µmol) instead of complex 1a and toluene as solvent.
Result: oily polyethylene was obtained. Activity: $5.0 \times 10^6$ g/mol·h·atm. Bromine number 40 g/100 g. Mn: 200,000 g/mol.

Example 58 (Solvent Hexane)

Repeat the procedure of example 39, the difference is that using complex 1j (5 µmol) instead of complex 1a and hexane as solvent.
Result: oily polyethylene was obtained. Activity: $1 \times 10^6$ g/mol·h·atm, Mn 125,000 g/mol.

Example 59 (Solvent Chlorobenzene)

Repeat the procedure of example 39, the difference is that using complex 1j (5 µmol) instead of complex 1a and chlorobenzene as solvent.
Result: oily polyethylene was obtained. Activity: $1 \times 10^6$ g/mol·h·atm, bromine number 50 g/100 g.

Example 60 (Solvent Dichloromethane)

Repeat the procedure of example 39, the difference is that using complex 1j (5 µmol) instead of complex 1a and DCM as solvent, the temperature is 20° C.
Result: oily polyethylene was obtained. Activity: $5 \times 10^6$ g/mol·h·atm, bromine number 30 g/100 g.

Example 61 (Co-Catalyst: MMAO)

Repeat the procedure of example 39, the difference is that using complex 1j (5 µmol) instead of complex 1a and add co-catalyst MMAO (0.30 mL, 1.9M).
Result: oily polyethylene was obtained. Activity: $6 \times 10^6$ g/mol·h·atm, Bromine number: 35.6 g/100 g. $^1$HNMR 200 Me/1000 $CH_2$. Mn 350,000 g/mol Example 62 (Co-Catalyst: MAO)

Repeat the procedure of example 39, the difference is that using complex 1j (5 umol) instead of complex 1a and add co-catalyst MAO (0.30 mL, 1.5M).
Result: oily polyethylene was obtained. Activity: $7.0 \times 10^6$ g/mol·h·atm, Bromine number: 37 g/100 g. $^1$HNMR 180 Me/1000 $CH_2$. Mn 400,000 g/mol Example 63 (80° C.)

Repeat the procedure of example 39, the difference is that the temperature is 80° C.

Result: oily polyethylene was obtained. Activity: $1 \times 10^6$ g/mol·h·atm, Bromine number 50 g/100 g. $^1$HNMR 480 Me/1000 $CH_2$. Mn: 1,000 g/mol.

Example 64 (20° C.)

Repeat the procedure of example, the difference is that the temperature is 20° C.
Result: oily polyethylene was obtained. Activity: $7 \times 10^6$ g/mol·h·atm, Bromine number 30.8 g/100 g. $^1$HNMR 120 Me/1000 $CH_2$. Mn: 5,000 g/mol.

Example 65 (Pressure 3 atm)

A 300 mL Parr autoclave is dried in vacuo at 120° C. overnight. Then at 80° C., it was purged with nitrogen and added DCE (100 mL), and co-catalyst $AlEt_2Cl$ (1.0 mL, 0.9M). The reaction was stirred for 10 min, and then added complex 1a (5 µmol). After that the autoclave is charged with ethylene (3 atm) immediately. After 30 min, ethylene was vented. The reaction mixture was concentrated and purified by silica gel column with petroleum ether. The filtrate was concentrated to obtain oily polyethylene. Activity: $6 \times 10^6$ g/mol·h·atm, bromine number 39.8 g/100 g. Mn 10,000 g/mol.

Example 66 (Pressure 5 atm)

Repeat the procedure of example 65, the difference is that the pressure of ethylene is 5 atm, the solvent is toluene, and the polymerization temperature is 100° C.
Result: oily polyethylene was obtained. Activity: $3 \times 10^6$ g/mol·h·atm, $^1$HNMR 100 Me/1000 $CH_2$. Mn: 20,000 g/mol.

Example 67 (Nickel Chloride)

Repeat the procedure of example 39, the difference is that using complex 1t instead of complex 1a and add MMAO (0.30 mL, 1.9M) as cocatalyst.
Result: oily polyethylene was obtained. Activity: $1 \times 10^6$ g/mol·h·atm.

Example 68 (Nickel Iodide)

Repeat the procedure of example 39, the difference is that using complex 1u instead of complex 1a and add MAO (0.30 mL, 1.5M) as co-catalyst.
Result: oily polyethylene was obtained. Activity: $1 \times 10^6$ g/mol·h·atm.

Example 69 (Benzyl Nickel)

Repeat the procedure of example 39, the difference is that using complex 1v instead of complex 1a.
Result: oily polyethylene was obtained. Activity: $5 \times 10^6$ g/mol·h·atm, $^1$HNMR 250 Me/1000 $CH_2$.

Example 70 (Nickel Perchlorate Hexahydrate)

A Schlenk flask (200 mL) was purged first with nitrogen three times and then vacuumized, and then purged with ethylene. Under the atmosphere of ethylene, 30 mL DCE, $Ni(ClO_4)_2$ (5 µmol) and L1a (5.0 µmol) were added, and the reaction was stirred for 2 h. Then co-catalyst $AlEt_2Cl$ (0.9M, 1.0 mL) was added, and the reaction mixture was stirred under 1 atm at 60° C. for 30 min. When the reaction completed, the ethylene was vented. The reaction mixture was concentrated and purified by silica gel column with petroleum ether. The filtrate was concentrated to obtain oily polyethylene. Activity: $1.5 \times 10^6$ g/mol·h·atm.

Example 71 (Nickel Trifluoromethanesulfonate)

Repeat the procedure of example 70, the difference is that using $Ni(OTf)_2$.

Result: oily polyethylene was obtained. Activity: $1.5 \times 10^6$ g/mol·h·atm.

Example 72 ((COD)N)

Repeat the procedure of example 70, the difference is that using Ni(COD).

Result: oily polyethylene was obtained. Activity: $1.0 \times 10^6$ g/mol·h·atm.

Example 73

Synthesis of Ligand L1w

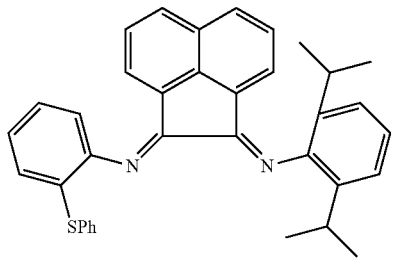

Following the procedure of example 1, Ligand L1w was obtained except that using 2-(phenylthio)aniline instead of aniline in the second step. $^1$H NMR (300 MHz, CDCl$_3$): δ=7.87-6.58 (18H, m), 3.00-2.66 (2H, m), 1.20-0.92 (12H, d); Anal. Calcd. C, 82.40; H, 6.15; N, 5.34. Found C, 82.41; H, 6.13; N, 5.16.

Example 74

Synthesis of Complex 1w

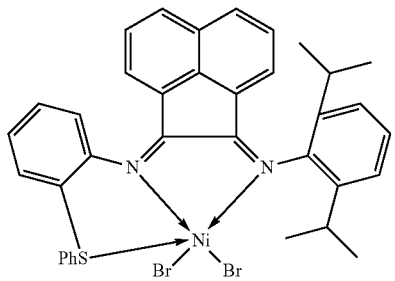

Figure 2:
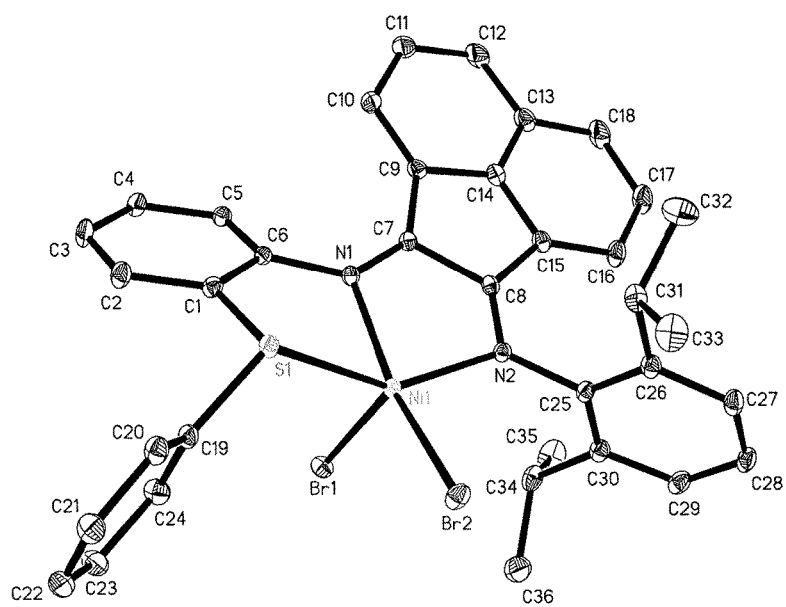
FIG. 2 shows the structure of the complex prepared in one example in the present invention.

Following the procedure of example 18, complex was obtained except that using ligand L1w instead of L1a. The structure of the complex is as FIG. 2. Anal. Calcd. For $C_{36}H_{32}Br_2N_2NiS$: C, 58.18; H, 4.34; N, 3.77. Found: C, 58.05; H, 4.49; N, 3.71.

Example 75

Repeat the procedure of example 39, except that using complex 1w instead of complex 1a for ethylene polymerization to obtain 2.5 g oily polyethylene Activity: $1.0 \times 10^6$ g/mol·h·atm.

Examples 78-82 is comparative examples using catalyst cited in the literature, only solid polyethylene was obtained using such catalyst under the same conditions as example 39, 63, 64, 57, 62.

Example 76

Synthesis of Ligand L1s (Comparative Ligand)

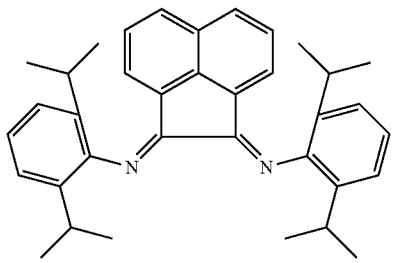 [SMILES: CC(C)c1cccc(C(C)C)c1/N=C1/C(=N/c2c(C(C)C)cccc2C(C)C)c2cccc3cccc1c23]

In a 100 mL egg-shaped flask, acenaphthoquinone (1.822 g, 10 mmol), 2,6-diisopropylaniline (4.0 mL, 21 mmol) and two drops of anhydrous acetic acid were added. The reaction was heated at reflux and monitored by TLC until ended. After the reaction was completed, the orange red diimine product was obtained by crystallizing from anhydrous methanol. $^1$H NMR (300 MHz, CDCl$_3$): δ=7.89 (2H, d), 7.36 (2H, t), 7.26 (6H, s), 6.64 (2H, d), 3.03 (4H, m), 1.24 (12H, d), 0.98 (12H, d).

Example 77

Synthesis of Complex 1s

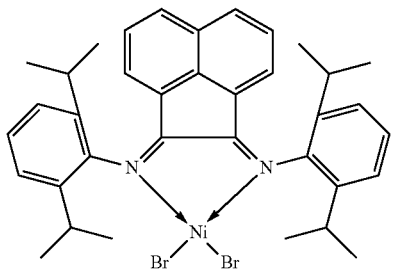

Following the procedure of example 18, a reddish brown complex was obtained except that using ligand L1s instead of L1a yield 80%. Anal. Calcd. For $C_{36}H_{40}Br_2N_2Ni$: C, 60.12; H, 5.61; N, 3.89. Found: C, 60.65; H, 5.87; N, 4.24.

Example 78 (Comparative with Example 39)

A Schlenk flask (200 mL) was purged first with nitrogen for 3 times, then vacuumized, and then purged with ethylene. Under the atmosphere of ethylene, 25 mL DCE and then co-catalyst $AlEt_2Cl$ (0.9M, 0.3 mL) were added. Under 1 atm, at 60° C., complex 1s (5 μmol) was added and the reaction mixture was stirred for 30 min. when the reaction completed, the ethylene was vented. The reaction mixture was poured into acidified ethanol. Then the solid polymer precipitated and was filtered. The solid was dried in vacuo to obtain 2.0 g solid polymer. Activity: $0.8 \times 10^6$ g/mol·h·atm.

Example 79 (Comparative with Example 63)

A Schlenk flask (200 mL) was purged first with nitrogen for 3 times, then vacuumized, and then purged with ethylene. Under the atmosphere of ethylene, 25 mL DCE and then co-catalyst $AlEt_2Cl$ (0.9M, 0.3 mL) were added. Under 1 atm, at 80° C., complex 1s (5 μmol) was added and the reaction mixture was stirred for 30 min. when the reaction completed, the ethylene was vented. The reaction mixture was poured into acidified ethanol. Then the solid polymer precipitated and was filtered. The solid was dried in vacuo to obtain 1.5 g solid polymer. Activity: $0.6 \times 10^6$ g/mol·h·atm.

Example 80 (Comparative with Example 64)

A Schlenk flask (200 mL) was purged first with nitrogen for 3 times, then vacuumized, and then purged with ethylene. Under the atmosphere of ethylene, 25 mL toluene and then co-catalyst $AlEt_2Cl$ (0.9M, 0.3 mL) were added. Under 1 atm, at 20° C., complex 1s (5 μmol) was added and the reaction mixture was stirred for 30 min. when the reaction completed, the ethylene was vented. The reaction mixture was poured into acidified ethanol. Then the solid polymer precipitated and filtered. The solid was dried in vacuo to obtain 7.5 g solid polymer. Activity: $3.0 \times 10^6$ g/mol·h·atm.

Example 81 (Comparative with Example 57)

A Schlenk flask (200 mL) was purged first with nitrogen for 3 times, then vacuumized, and then purged with ethylene. Under the atmosphere of ethylene, 25 mL toluene and then co-catalyst $AlEt_2Cl$ (0.9M, 0.3 mL) were added. Under 1 atm, at 60° C., complex 1s (5 μmol) was added and the reaction mixture was stirred for 30 min. when the reaction completed, the ethylene was vented. The reaction mixture was poured into acidified ethanol. Then the solid polymer precipitated and filtered. The solid was dried in vacuo to obtain 1.0 g solid polymer. Activity: $0.4 \times 10^6$ g/mol·h·atm.

Example 82 (Comparative with Example 62)

A Schlenk flask (200 mL) was purged first with nitrogen for 3 times, then vacuumized, and then purged with ethylene. Under the atmosphere of ethylene, 25 mL DCE and then co-catalyst MAO (1.5 M, 0.3 mL) were added. Under 1 atm, at 60° C., complex 1s (5 μmol) was added and the reaction mixture was stirred for 30 min. when the reaction completed, the ethylene was vented. The reaction mixture was poured into acidified ethanol. Then the solid polymer precipitated and filtered. The solid was dried in vacuo to obtain 2.0 g solid polymer. Activity: $0.8 \times 10^6$ g/mol·h·atm, there is no oily polyethylene in the filtrate.

Example 83

Synthesis of Ligand L1x

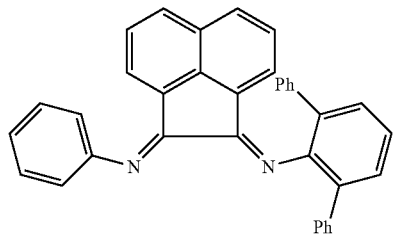 [SMILES: c1ccc(/N=C2/C(=N/c3c(-c4ccccc4)cccc3-c3ccccc3)c3cccc4cccc2c34)cc1]

Following the procedure of example 1, except that using 2,6-diphenylaniline instead of 2,6-diisopropylaniline in the first step, ligand L1x was obtained. Anal. Calcd. C, 89.23; H, 4.99; N, 5.78. Found C, 82.50; H, 6.24; N, 5.30.

Example 84

Synthesis of Complex 1x

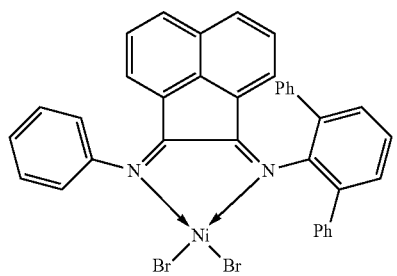

Following the procedure of example 18, except that using L1x instead of L1a, complex 1x was obtained. Anal. Calcd. C, 61.50; H, 3.44; N, 3.98. Found C, 61.75; H, 3.78; N, 4.20.

Example 85

Following the procedure of example 39, except that using complex 1x instead of 1a, 7.6 g oily polyethylene was obtained. Activity: $3.1 \times 10^6$ g/mol·h·atm, $^1$HNMR 160 Me/1000 $CH_2$.

Example 86

Synthesis of Ligand 1y

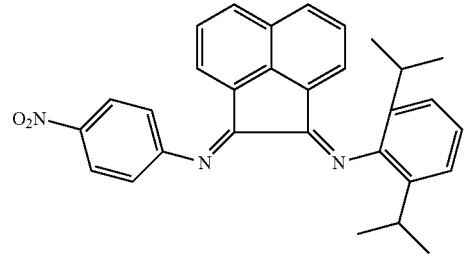 [SMILES: CC(C)c1cccc(C(C)C)c1/N=C1/C(=N/c2ccc([N+](=O)[O-])cc2)c2cccc3cccc1c23]

Following the procedure of example 1, except that using 4-nitroaniline instead of aniline, L1y was obtained. $^1$H NMR (300 MHz, $CDCl_3$): δ=8.33-6.48 (13H, m), 2.91-2.43 (2H, m), 1.15-0.81 (12H, m); $^{13}$C NMR (75 MHz, $CDCl_3$): δ=161.0, 157.7, 146.9, 144.4, 141.4, 135.3, 134.0, 131.1, 129.9, 129.1, 128.8, 127.6, 125.5, 124.7, 124.5, 123.9, 123.8, 123.6, 123.4, 123.3, 123.2, 121.8, 120.6, 118.8, 117.8, 77.0, 28.3, 23.5, 23.4, 23.3, 22.4.

Example 87

Synthesis of Complex 1y

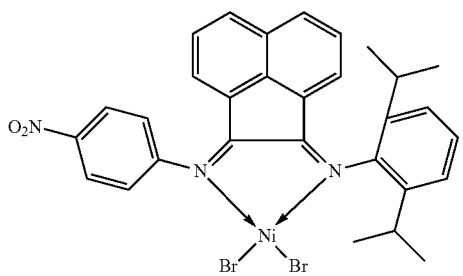

Following the procedure of example 18, except that using ligand L1y instead of L1a, and complex 1y was obtained. Anal. Calc. C, 52.98; H, 4.00; N, 6.18. Found C, 53.33; H, 4.34; N, 6.04.

Example 88

Following the procedure of example 39, except that using complex 1y instead of 1a, using propene instead of ethylene and 0.8 g oily polypropylene was obtained. Activity: 3.2× $10^6$ g/mol·h·atm, $^1$HNMR 260 Me/1000 $CH_2$. Mn: 1500 g/mol.

Example 89

Synthesis of ligand 1z

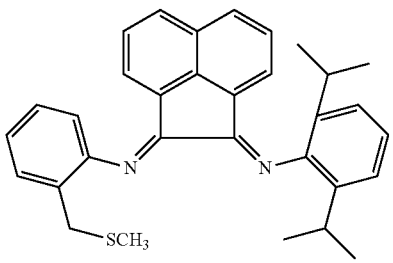 [SMILES: CSCc1ccccc1/N=C1/C(=N/c2c(C(C)C)cccc2C(C)C)c2cccc3cccc1c23]

Following the procedure of example 1, except that using 2-((methylthio)methyl)aniline instead of aniline, and L1z was obtained. $^1$H NMR (300 MHz, $CDCl_3$): δ=8.19-6.59 (13H, m), 3.75 (2H, s), 3.04 (2H, m), 1.89 (3H, s), 1.24-0.97 (12H, m); Anal. Calcd. C, 80.63; H, 6.77; N, 5.88. Found C, 80.55; H, 6.72; N, 5.75.

Example 90

Synthesis of Complex 1z

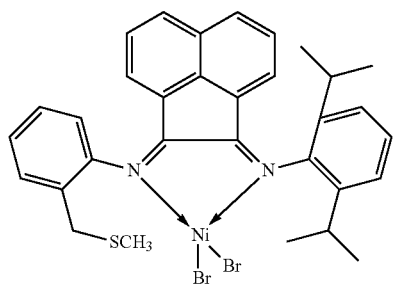

Following the procedure of example 18, except that using ligand L1z instead of L1a, and complex 1z was obtained. Anal. Calc. C, 55.29; H, 4.64; N, 4.03. Found C, 54.99; H, 4.55; N, 3.94.

Example 91

Following the procedure of example 39, except that using complex 1z instead of 1a and using but-2-ene instead of ethylene, and 2.5 g highly branched oily polybutylene was obtained. Activity: 1×$10^6$ g/mol·h·atm.

The results are summarized in Table 1.

TABLE 1

| Compound | Y and Z together forming | $R^1$ | $R^2$ | $R^3$ | $R^4$ | $R^5$ | $R^6$ | $R^7$ | Complex | Activity $10^6$ g/mol · h · atm (product form) |
|---|---|---|---|---|---|---|---|---|---|---|
| 1 | Naphthyl | $CH(CH_3)_2$ | $CH(CH_3)_2$ | H | H | H | H | H | 1a | 3.0 (oil) |
| 2 | Naphthyl | $CH(CH_3)_2$ | $CH(CH_3)_2$ | Cl | Cl | H | H | H | 1b | 7.0 (oil) |
| 3 | Naphthyl | $CH(CH_3)_2$ | $CH(CH_3)_2$ | Br | Br | H | H | H | 1c | 9.0 (oil) |
| 4 | Naphthyl | $CH_3$ | $CH_3$ | Cl | Cl | H | H | H | 1d | 1.0 (oil) |
| 5 | Naphthyl | $CH(CH_3)_2$ | $CH(CH_3)_2$ | H | H | H | $OCH_3$ | H | 1e | 2.0 (oil) |
| 6 | Naphthyl | $CH(CH_3)_2$ | $CH(CH_3)_2$ | H | H | H | $N(CH_3)_2$ | H | 1f | 2.0 (oil) |
| 7 | Naphthyl | $CH(CH_3)_2$ | $CH(CH_3)_2$ | H | H | H | Cl | H | 1g | 2.0 (oil) |
| 8 | Naphthyl | $CF_3$ | Br | $CH(CH_3)_2$ | H | Br | H | H | 1h | 1.0 (oil) |
| 9 | phenanthryl | $CH(CH_3)_2$ | $CH(CH_3)_2$ | Cl | Cl | H | H | H | 1i | 50 (oil) |
| 10 | phenanthryl | $CH(CH_3)_2$ | $CH(CH_3)_2$ | Br | Br | H | H | H | 1j | 4.0 (oil) |
| 11 | Z: phenyl Y: $CH_3$ | Cl | Cl | $CH(CH_3)_2$ | $CH(CH_3)_2$ | H | H | H | 1k | 5.0 (oil) |
| 12 | Z: phenyl Y: $CH_3$ | Br | Br | $CH(CH_3)_2$ | $CH(CH_3)_2$ | H | H | H | 1l | 6.0 (oil) |
| 13 | Naphthyl | $CF_3$ | Br | $CF_3$ | H | Br | H | H | 1m | 4.5 (oil) |
| 14 | Naphthyl | $CF_3$ | Br | t-Bu | H | Br | H | H | 1n | 8.0 (oil) |
| 15 | Naphthyl | $CH(CH_3)_2$ | $CH(CH_3)_2$ | H | H | H | $CF_3$ | H | 1o | 2.0 (oil) |
| 16 | Naphthyl | $CH(CH_3)_2$ | $CH(CH_3)_2$ | H | H | H | H | $CF_3$ | 1p | 2.0 (oil) |
| 17 | Naphthyl | $CH(CH_3)_2$ | $CH(CH_3)_2$ | $PhOCH_2$ | H | H | H | H | 1q | 1.0 (oil) |
| 18 | Naphthyl | $CH(CH_3)_2$ | $CH(CH_3)_2$ | $PhOCH_2$ | H | H | H | H | 1r (X is $CH_3$) | 8.0 (oil) |
| 19* | Naphthyl | $CH(CH_3)_2$ | $CH(CH_3)_2$ | $CH(CH_3)_2$ | $CH(CH_3)_2$ | H | H | H | 1s | 0.8 (solid) |
| 20 | Naphthyl | $CH(CH_3)_2$ | $CH(CH_3)_2$ | PhS— | H | H | H | H | 1w | 1.0 (oil) |
| 21 | Naphthyl | phenyl | phenyl | H | H | H | H | H | 1x | 3.1 (oil) |

TABLE 1-continued

| Compound | Y and Z together forming | R$^1$ | R$^2$ | R$^3$ | R$^4$ | R$^5$ | R$^6$ | R$^7$ | Complex | Activity 10$^6$ g/mol · h · atm (product form) |
|---|---|---|---|---|---|---|---|---|---|---|
| 22 | Naphthyl | CH(CH$_3$)$_2$ | CH(CH$_3$)$_2$ | H | H | H | NO$_2$ | H | 1y | 3.2 (oil) |
| 23 | Naphthyl | CH(CH$_3$)$_2$ | CH(CH$_3$)$_2$ | H | CH$_3$SCH$_2$ | H | H | H | 1z | 1.0 (oil) |

*Compound 19 as a comparative compound.

Preparing Highly Branched Oily Alkane by Hydrogenation (Oily Alkane Mixture)

Example 92

In a 50 mL egg-shaped flask, highly branched oily polyethylene (2.5 g) obtained in example 47, Pd/C (50 mg) and n-hexane (10 mL) were added. The flask was then purged with hydrogen for three times and at the atmospheric pressure, the reaction was stirred overnight at room temperature. Stop the hydrogenation until the raw material was hydrogenated completely determined by $^1$HNMR. The reaction mixture was filtered through silica gel column. The filtrate was concentrated to obtain highly branched oily alkane. Bromine number: 0.31 g/100 g. $^1$HNMR 230 Me/1000 CH$_2$. VI 261. Kinetic viscosity (100° C.): 7.9 cSt. The $^{13}$CNMR spectra is shown as FIG. 1. The molecular weight is about 110,000 g/mol. Pour point is −15° C., flash point is 194° C., Evaporation loss is 3.8% W/W.

Example 93 (Neat)

In a 50 mL egg-shaped flask, highly branched oily polyethylene (2.5 g) obtained in example 47, and Pd/C (50 mg) were added. The flask was then purged with hydrogen for three times and at the atmospheric pressure, the reaction was stirred overnight at room temperature. Stop the hydrogenation until the raw material was hydrogenated completely determined by $^1$HNMR. The reaction mixture was filtered through silica gel column. The filtrate was concentrated to obtain highly branched oily alkane. Bromine number: 0.33 g/100 g. $^1$HNMR 260 Me/1000 CH$_2$.

Example 94

Repeat the procedure of example 92, except that using Pd(OH)$_2$ instead of Pd/C.
Result: oily polyethylene was obtained, bromine number: 0.39 g/100 g.

Example 95

Repeat the procedure of example 92, except that using oily polyethylene produced in example 48 as the substrate to be hydrogenated.
Result: highly branched oily alkane was obtained, bromine number: 0.38 g/100 g. $^1$HNMR 240 Me/1000 CH$_2$. VI: 300.

Example 96

Repeat the procedure of example 92, except that using oily polyethylene produced in example 41 instead.
Result: highly branched oily alkane was obtained, bromine number: 0.36 g/100 g.

Example 97

Repeat the procedure of example 39, except that using propylene instead of ethylene to obtain oily polypropylene. Then repeat the procedure of example 92, except that using the oily polypropylene instead.
Result: highly branched oily alkane was obtained, bromine number: 0.10 g/100 g. Pour point: −40° C. Flash point: 190° C.

Example 98

Repeat the procedure of example 39, except that using butene instead of ethylene to obtain oily polybutene. Then under the same condition as example 92, hydrogenate the oily polybutene to obtain highly branched oily alkane. Bromine number: 0.49 g/100 g.

Example 99

Repeat the procedure of example 39, except that using complex 1i to catalyze the polymerization of 1-butene instead of 1a, to obtain 3.2 g oily polybutylene. Then under the same condition as example 92, hydrogenate the oily polybutylene to obtain highly branched oily alkane.
Bromine number: 0.43 g/100 g. Pour point: −15° C. Flash point: 200° C. VI: 195.

Example 100

Repeat the procedure of example 39, except that using complex 1a to catalyze the copolymerization of ethylene and 1-butene to obtained 5.8 g oily polymer. Then under the same condition as example 92, hydrogenate the oily polymer to obtain highly branched oily alkane.
Bromine number: 0.31 g/100 g. Pour point: −17° C. Flash point: 193° C. VI: 186.

Example 101

Repeat the procedure of example 47, except that reacting ethylene with the catalyst for polymerization and purging hydrogen simultaneously. After the hydrogenation completed, filter the reaction mixture and concentrate the filtrate to obtain highly branched oily alkane.
Bromine number: 0.48 g/100 g. $^1$HNMR 320 Me/1000 CH$_2$. VI: 189. Pour point: −26° C. Flash point: 190° C.

Example 102

Repeat the procedure of example 47, except that after reacting ethylene with the catalyst for polymerization for 30 min, the reaction mixture was added Pd/C (50 mg) without processing and purged with hydrogen. After the hydrogenation completed, filter the reaction mixture and concentrate the filtrate to obtain highly branched oily alkane. $^1$HNMR: 260 Me/1000 CH$_2$.

Example 103

Repeat the procedure of example 47, except that after reacting ethylene with the catalyst for polymerization for 30 min, the reaction was directly purged with hydrogen without processing and reacted under the atmosphere of hydrogen until completed. The reaction mixture was filtered and the filtrate was concentrated to obtain highly branched oily alkane. Bromine number: 0.34 g/100 g.

Example 104

A 300 mL Parr autoclave is dried in vacuo in an oil bath at 120° C. overnight. It was purged with nitrogen for three times, and then in an oil bath at 60° C., DCE (50 mL) and MMAO (1.0 mL) were added. Then under the atmosphere of hydrogen (0.5 atm), catalyst 1b (5 μmol) was added. Then ethylene was purged and the reaction was conducted for 30 min. After that, the reaction was cooled and the autoclave was opened. The reaction mixture was filtered and the filtrate was concentrated to obtain 3.0 g oily polyethylene. Bromine number 0.48 g/100 g. $^1$HNMR: 230 Me/1000 $CH_2$. Pour point: −23° C.

Example 105

A 300 mL Parr autoclave is dried in vacuo in an oil bath at 120° C. overnight. It was purged with nitrogen for three times, and then in an oil bath at 80° C., DCE (50 mL) and MMAO (1.0 mL) were added. Then under the atmosphere of hydrogen (0.5 atm), catalyst 1b (5 μmol) was added. Then ethylene was purged and the reaction was conducted for 30 min. After that, the reaction was cooled and the autoclave was opened. The reaction mixture was filtered and the filtrate was concentrated to obtain 1.5 g oily polyethylene. Bromine number 0.28 g/100 g. $^1$HNMR: 300 Me/1000 $CH_2$.

Example 106

A 300 mL Parr autoclave is dried in vacuo in an oil bath at 120° C. overnight. It was purged with nitrogen for three times, and then in an oil bath at 80° C., DCE (50 mL) and $AlEt_2Cl$ (1.0 mL) were added. Then under the atmosphere of hydrogen (0.5 atm), catalyst 1b (5 umol) was added. Then ethylene was purged and the reaction was conducted for 30 min. After that, the reaction was cooled and the autoclave was opened. The reaction mixture was filtered and the filtrate was concentrated to obtain 1.3 g oily polyethylene. Bromine number 0.37 g/100 g. $^1$HNMR: 450 Me/1000 $CH_2$. Pour point: −32° C.

Example 107

A 300 mL Parr autoclave is dried in vacuo in an oil bath at 120° C. overnight. It was purged with nitrogen for three times, and then in an oil bath at 45° C., 50 mL of oily polyethylene (Mv: 1500 g/mL) and MMAO (1.0 mL) were added. Then under the atmosphere of hydrogen (0.5 atm), catalyst 1c (5 μmol) was added. Then the reaction was purged with ethylene and conducted for 30 min. After that, the reaction was cooled and the autoclave was opened. The reaction mixture was filtered and the filtrate was concentrated to obtain 4.5 g oily polyethylene. Bromine number 0.39 g/100 g. $^1$HNMR 320 Me/1000 $CH_2$.

Example 108

Repeat the procedure of example 92, except that using oily polyethylene obtained in example 63 as the substrate for hydrogenation.

Result: highly branched oily alkane was obtained, bromine number: 0.25 g/100 g. $^1$HNMR 490 Me/1000 $CH_2$.

Example 109

Repeat the procedure of example 92, except that using oily polyethylene obtained in example 49 as the substrate for hydrogenation.
Result: highly branched oily alkane was obtained, bromine number: 0.14 g/100 g. $^1$HNMR 110 Me/1000 $CH_2$.

Example 110

Repeat the procedure of example 39, except that using complex 1a to catalyze the copolymerization of ethylene and hex-5-en-1-ol to produce oily copolymer 9.0 g.
Then under the same condition as example 92, hydrogenate the oily polymer to obtain highly branched oily alkane with alcoholic hydroxyl group. Bromine number: 0.30 g/100 g. Pour point: −30° C. Flash point: 193° C. VI: 180.

Example 111

Repeat the procedure of example 39, except that using complex 1a to catalyze the copolymerization of ethylene and dec-9-en-1-ol to produce oil copolymer 12.1 g.
Then under the same condition as example 92, hydrogenate the oily polymer to obtain highly branched oily alkane with alcoholic hydroxyl group. Pour point: −19° C.

Example 112

Repeat the procedure of example 39, except that using complex 1a to catalyze the copolymerization of ethylene and methyl dec-9-enoate to obtain oily polymer 5.6 g.
Then under the same condition as example 92, hydrogenate the oily polymer to obtain highly branched oily alkane with ester group. Pour point: −29° C. VI: 190. Flash point: 198° C.

There is no specific number of methyl groups in the oily alkane polymer in example 92-112, it is determined that, the number of corresponding methyl groups per 1000 methylene is 160 to 350.

Example 113

Refer to ASTM D97 (petroleum-based oil's pour point standard) to measure the product pour point.
Refer to ASTM D1500 standard method to measure chroma.
Refer to ASTM D4052 standard method to measure density at 15.6° C.
Refer to ASTM D445 standard method to measure kinematic viscosity at 100° C. and 40° C.
Refer to ASTM D92 standard method to measure bromine number.
Refer to ASTM D1159 standard method to determine flash point.
Refer to ASTM D664 standard method to determine acidity.
Wherein, as testing pour point and flash point needs more samples, enlarge the scale of polymerization under the same conditions as in various examples to obtain the test sample.
The results are shown in Table 2. The results show that the pour point, flash point, chroma, evaporation loss of the highly branched oil alkane of the present invention is equivalent to the commercially available PAO or Group III base oil, but the viscosity index is higher than the existing products, and can remain the viscosity in a larger temperature range and is more suitable for lubricant base oil.

TABLE 2 test results of Performance

| example | chroma | viscosity (cSt 100° C.) | viscosity (cSt 40° C.) | Viscosity index | Pour point (° C.) | Flash point ° C.) | Evaporation loss (% W/W) |
|---|---|---|---|---|---|---|---|
| 92 | <0.5 | 7.9 | 29.3 | 261 | −15 | 194 | 3.8 |
| 93 | <0.5 | 7.9 | 29.3 | 261 | −15 | 194 | |
| 94 | <0.5 | 7.9 | 29.3 | 261 | −15 | 194 | |
| 95 | <0.5 | 8.5 | 30.2 | 300 | −17 | 200 | |
| 97 | <0.5 | 4.5 | 20.1 | 150 | −40 | 190 | |
| 98 | <0.5 | 7.4 | 35.7 | 180 | | | |
| 99 | <0.5 | 8.4 | 40.1 | 195 | −15 | 200 | |
| 100 | <0.5 | 7.0 | 32.4 | 186 | −17 | 193 | |
| 101 | <0.5 | 4.5 | 18.2 | 189 | −26 | 190 | |
| 102 | <0.5 | 7.9 | 29.3 | 261 | −15 | 194 | |
| 103 | <0.5 | 7.9 | 29.3 | 261 | −15 | 194 | |
| 104 | <0.5 | 4.4 | 17.5 | 190 | −23 | | |
| 105 | <0.5 | 4.3 | 16.8 | 188 | | | |
| 106 | <0.5 | 4.1 | 16.3 | 180 | −32 | | 3.9 |
| 107 | <0.5 | 7.0 | 28.6 | 230 | | | |
| 108 | <0.5 | 4.6 | 19.1 | 179 | | | |
| 110 | <0.5 | | | 180 | −30 | 193 | |
| 111 | <0.5 | | | | −19 | | |
| 112 | <0.5 | | | 190 | −29 | 198 | |
| PAO(Controle) | <0.5 | 8.0 | 48.0 | 139 | −48 | | 4.1 |
| Group III base oil (Controle) | <0.5 | 4.0 | | 120-130 | −18~−20 | | 13-14 |

Preparation of Lubricant

Example 114

Following the procedure of example 92, enlarge the polymerization to obtain oil products to be used as base oil. Basing on the quality of the base oil, 0.2 wt %-0.5 wt % of methyl acrylate copolymer or a polyacrylate was mixed with base oil to produce the lubricant. The pour point of the lubricant is −32° C. to −40° C.

Example 115

Following the procedure of example 92, enlarge the polymerization to obtain oil products to be used as base oil. Copolymer of long chain alkyl acrylate and acrylonitrile (500 mg/L oil products) was mixed with base oil to produce the lubricant. The pour point of the lubricant decreased to −20° C.~−30° C.

Example 116

Following the procedure of example 97, enlarge the polymerization to obtain oil products to be used as base oil. Basing on the quality of the base oil, 0.02 wt % 2,6-di-tert-butyl-α-dimethylamino-4-methylphenol as antioxidation, and 0.5 wt %-2 wt % the dodecencyl succinic salts of heptadecenyl imidazoline or 0.5 wt %-4 wt % barium dinonyl naphthalene sulfonate, and the condensate of amine and epoxide were mixed with base oil to produce the antirust and antioxidative lubricant.

Example 117

Following the procedure of example 97, enlarge the polymerization to obtain oil products to be used as base oil. Basing on the quality of the base oil, 1 wt %-5 wt % multialkenyl succimide or monoalkenyl succimide or dialkenyl succimide as a dispersant, 0.8 wt %-1.3 wt % synthetic calcium sulfonate with high base number or 2 wt %-3 wt % calcium alkylsalicylate as a detergent, 0.1 wt %-0.5 wt % silicone grease as a defoaming agent, 0.4 wt %-0.6 wt % the condensate of amine and epoxide as anticreaming agent were mixed with base oil to produce a lubricant.

Example 118

Following the procedure of example 90, enlarge the polymerization to obtain oil products to be used as base oil. Basing on the quality of the base, 0.1 wt %-1.0 wt % alkyl naphthalene was mixed with base oil to produce a lubricant.

Example 119

Following the procedure of example 97, enlarge the polymerization to obtain oil products to be used as base oil. Basing on the quality of the base, 0.3 wt % phosphate as a friction modifier was mixed with base oil to produce a lubricant.

Example 120

Following the procedure of example 97, enlarge the polymerization to obtain oil products to be used as base oil. Basing on the quality of the base, 0.2 wt %-0.5 wt % zinc salt of dialkyl phosphorodithioic acid as a antioxidant corrosion inhibitor was mixed with base oil to produce a lubricant.

Example 121

Following the procedure of example 97, enlarge the polymerization to obtain oil products to be used as base oil. Basing on the quality of the base, 2 wt %-10 wt % of ethylene glycol oleate as an oiliness agent was mixed with base oil to produce a lubricant.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:

1. An oily alkane mixture prepared by the following steps:
   (a) catalyzing ethylene polymerization in the presence of
      (1) a catalyst comprising one or more complex(es); and
      (2) a cocatalyst comprising one or more alkyl aluminum reagents, thereby forming an oily highly branched polyethylene;
   (b) hydrogenating the oily highly branched polyethylene in the presence of a reduction catalyst;
   wherein each of said one or more complex(es) independently comprises one or more salt(s), wherein each of said one or more salt(s) independently comprises a compound of formula I and one or more divalent metal(s) selected from the group consisting of nickel, palladium and a combination thereof;

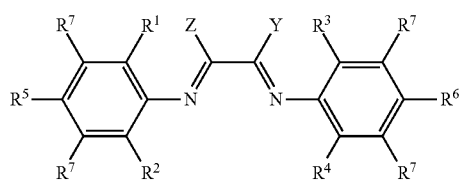

I wherein,

Z is hydrogen, $C_1$-$C_4$ alkyl, $C_1$-$C_4$ haloalkyl, or unsubstituted or substituted phenyl;

Y is unsubstituted or substituted phenyl;

or Z and Y are combined with the adjacent carbon atom to form an unsubstituted or substituted acenaphthyl, phenanthryl, or $C_5$-$C_8$ cycloalkyl, wherein each of the substituted phenyl, acenaphthyl, phenanthryl or cycloalkyl independently has 1 to 5 substituents selected from the group consisting of halogen, $C_1$-$C_4$ alkyl, and $C_1$-$C_4$ haloalkyl;

$R^1$ and $R^2$ are independently H, halogen, $C_1$-$C_8$ alkyl, $C_1$-$C_8$ haloalkyl, unsubstituted or substituted phenyl, —O—$R_a$, —$CH_2$—O—$R_a$, —$SR_b$, or —$CH_2$—S—$R_b$, wherein $R_a$ and $R_b$ are independently $C_1$-$C_8$ alkyl or unsubstituted or substituted phenyl;

$R^3$ and $R^4$ are independently H, halogen, $C_1$-$C_8$ haloalkyl, —O—$R_a$, —$CH_2$—O—$R_a$, —$SR_b$, or —$CH_2$—S—$R_b$; of $R^1$, $R^2$, $R^3$ and $R^4$, $R^1 \neq (R^3$ and $R^4)$ and/or $R^2 \neq (R^3$ and $R^4)$ and each substituted phenyl independently has 1 to 5 substituents selected from the group consisting of halogen, $C_1$-$C_4$ alkyl, and $C_1$-$C_4$ haloalkyl; and $R^5$, $R^6$ and $R^7$ are independently halogen, nitro, hydrogen, $C_1$-$C_8$ alkyl, $C_1$-$C_8$ haloalkyl, —O—$R_a$, or —$CH_2$—O—$R_a$; and wherein the oily alkane mixture comprises an oily alkane having a structure of $R_8R_9CH(CH_2)_n$, $CHR_{10}R_{11}$ or $R_8R_9R_{10}C(CH_2)_nCR_{10}R_{11}R_{12}$; wherein each $R_8$-$R_{12}$ independently has a structure of $R_{13}R_{14}CH(CH_2)_m$ $CHR_{15}R_{16}$ or $R_{13}R_{14}R_{15}C(CH_2)_nCR_{15}R_{16}R_{17}$; wherein each $R_{13}$-$R_{17}$ independently has a structure of $R_{18}R_{19}CH(CH_2)_xCHR_{20}R_{21}$ or $R_{18}R_{19}R_{20}C(CH_2)_x$ $CR_{20}R_{21}R_{22}$; wherein each $R_{18}$-$R_{22}$ is independently hydrogen or a straight-chain or branched-chain alkane; and wherein n, m, and x are each independently an integer from 1-100.

2. The oily alkane mixture of claim 1 having:
   (a) a viscosity index from 100 to 300;
   (b) a pour point from −50 to −10° C.; and
   (c) a bromine number <0.5 g/100 g.

3. The oily alkane mixture of claim 1, wherein the cocatalyst comprises di ethyl aluminum chloride, ethyl aluminum dichloride, or a combination thereof; wherein step (a) is carried out at a temperature from 0-100° C. and a pressure from 0.1-3 MPa; and wherein the molar ratio of aluminum in the cocatalyst to aluminum in the catalyst is from 10-5000.

4. The oily alkane mixture of claim 1, wherein the oily highly branched polyethylene comprises 100-500 methyl per 1000 methylene ($CH_2$).

5. The oily alkane mixture of claim 1, wherein the oily highly branched polyethylene comprises about 100-300 alkyl chains per 1000 methylene, and wherein per each 100 methyl branched chains there are 50-100 ethyl branched chains, 5-20 propyl branched chains, 30-80 butyl branched chains, 5-20 pentyl branched chains, and 50-100 hexyl or longer branched chains.

6. The oily alkane mixture of claim 1, wherein the one or more alkyl aluminum reagents comprise alkyl aluminoxanes, diethylaluminum chloride, ethyl aluminum dichloride, or a combination thereof.

7. The oily alkane mixture of claim 1, wherein step (a) is carried out at a temperature from 0-100° C. and a pressure from 0.1-3 MPa.

8. The oily alkane mixture of claim 1, wherein the molar ratio of aluminum in the cocatalyst to aluminum in the catalyst is from 10-5000.

9. The oily alkane mixture of claim 1, wherein step (a) is conducted in toluene, n-hexane, dichloromethane, 1,2-dichloroethane, chlorobenzene, tetrahydrofuran or a combination thereof.

10. The oily alkane mixture of claim 1, wherein the reduction catalyst comprises Pd/C, Pd(OH)$_2$, PtO$_2$, rhodium, nickel or ruthenium.

* * * * *